United States Patent
Stern

(10) Patent No.: US 10,610,666 B2
(45) Date of Patent: Apr. 7, 2020

(54) MULTI-FILAMENT CATHETER

(71) Applicant: Covidien LP, Mansfield, MA (US)

(72) Inventor: George Stern, Irvine, CA (US)

(73) Assignee: Covidien LP, Mansfield, MA (US)

( * ) Notice: Subject to any disclaimer, the term of this patent is extended or adjusted under 35 U.S.C. 154(b) by 820 days.

(21) Appl. No.: 14/979,766

(22) Filed: Dec. 28, 2015

(65) Prior Publication Data

US 2017/0182290 A1    Jun. 29, 2017

(51) Int. Cl.
*A61M 25/00* (2006.01)
*A61F 2/966* (2013.01)

(52) U.S. Cl.
CPC ...... *A61M 25/0053* (2013.01); *A61M 25/005* (2013.01); *A61M 25/0012* (2013.01); *A61M 25/0054* (2013.01); *A61F 2/966* (2013.01); *A61M 2025/0063* (2013.01)

(58) Field of Classification Search
CPC .......... A61M 25/0053; A61M 25/0012; A61M 25/005; A61M 25/0054
See application file for complete search history.

(56) References Cited

U.S. PATENT DOCUMENTS

| | | |
|---|---|---|
| 4,764,324 A | 8/1988 | Burnham |
| 4,932,419 A | 6/1990 | de Toledo |
| 5,380,304 A | 1/1995 | Parker |
| 5,429,597 A | 7/1995 | DeMello et al. |
| 5,695,483 A | 12/1997 | Samson |
| 5,951,539 A | 9/1999 | Nita et al. |
| 5,957,910 A | 9/1999 | Holden, II et al. |
| 7,713,259 B2 | 5/2010 | Gosiengfiao et al. |
| 7,905,877 B1 * | 3/2011 | Jimenez ............ A61M 25/0012 604/525 |
| 7,955,313 B2 * | 6/2011 | Boismier ................ A61L 29/02 604/524 |
| 7,959,660 B2 | 6/2011 | Lentz |
| 8,366,699 B2 | 2/2013 | Jimenez et al. |
| 2002/0001441 A1 | 1/2002 | Avellanet |
| 2004/0089969 A1 | 5/2004 | Willard |
| 2007/0255105 A1 | 11/2007 | Ochi et al. |
| 2008/0262471 A1 | 10/2008 | Warnock |
| 2014/0083969 A1 | 3/2014 | Porter |
| 2014/0135736 A1 | 5/2014 | Hebert |
| 2015/0100043 A1 | 4/2015 | Govari et al. |
| 2015/0258306 A1 | 9/2015 | Plassman et al. |

FOREIGN PATENT DOCUMENTS

| | | |
|---|---|---|
| WO | 9856448 A1 | 12/1998 |
| WO | 2015063781 A1 | 5/2015 |

OTHER PUBLICATIONS

Extended Search Report from counterpart European Application No. 16205557.8, dated May 16, 2017, 8 pp.

(Continued)

*Primary Examiner* — Ashley L Fishback

(74) *Attorney, Agent, or Firm* — Shumaker & Sieffert, P.A.

(57) ABSTRACT

In some examples, a catheter includes an elongated body including a structural support layer comprising at least two filaments of different materials wound longitudinally adjacent to each other to define a coil structure, and an outer jacket positioned over the structural support layer.

26 Claims, 6 Drawing Sheets

(56) References Cited

OTHER PUBLICATIONS

Examination Report from counterpart European Application No. 16205557.8, dated Mar. 8, 2018, 6 pp.
Response to Examination Report dated Mar. 8, 2018, from counterpart European Application No. 16205557.8, filed Jul. 6, 2018, 5 pp.
Intent to Grant dated Sep. 5, 2018, from counterpart European Application No. 16205557.8, 55 pp.
"Capabilities,"Corpus Medical INC, accessed from http://www.corpusmed.com/capabilites, date accessed Jun. 4, 2015, 2 pp.

* cited by examiner

MULTI-FILAMENT CATHETER

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, the disclosure describes examples catheters that include a plurality of filaments (e.g., coils members) wound longitudinally adjacent to each other and positioned between an inner liner and outer jacket of the catheter body. The plurality of filaments may include different materials designed to tailor the structural characteristics of the elongated body to, for example, increase any one or more of the flexibility, strength, torqueability, and maneuverability of the catheter through the vasculature of a patient. This disclosure also describes example methods of forming catheters that include a plurality of filaments wound longitudinally adjacent to each other and methods of using such catheters.

Clause 1: In one example, a catheter including an elongated body including a first coil member; a second coil member interspaced with the first coil member, the first and second coil members including different materials; and an outer jacket positioned over the first and second coil members.

Clause 2: In some examples of the catheter of clause 1, wherein at least one turn of the second coil member is positioned between adjacent turns of the first coil member.

Clause 3: In some examples of the catheter of clause 1, wherein the first coil member contacts the second coil member.

Clause 4: In some examples of the catheter of clause 1, wherein turns of the first coil member and turns of the second coil member are longitudinally offset from each other.

Clause 5: In some examples of the catheter of clause 4, wherein the offset defines a first coil spacing along a proximal portion of the elongated body and a second coil spacing along a distal portion of the elongated body, the second coil spacing being different than the first coil spacing.

Clause 6: In some examples of the catheter of clause 5, wherein the first coil spacing is less than the second coil spacing.

Clause 7: In some examples of the catheter of clause 1, wherein the first coil member and the second coil member are wound in a same direction.

Clause 8: In some examples of the catheter of clause 1, wherein the first coil member and the second coil member have substantially same pitches.

Clause 9: In some examples of the catheter of clause 1, wherein the first and second coil members have different pitches.

Clause 10: In some examples of the catheter of clause 1, wherein the catheter includes a plurality of coil members, the plurality including the first and second coil members, and further including at least one additional coil member formed from a same material as the first coil member.

Clause 11: In some examples of the catheter of clause 1, wherein the second coil member is interspaced with only a portion of the first coil member.

Clause 12: In some examples of the catheter of clause 1, wherein at least one of the first coil member or the second coil member includes a flat-wire.

Clause 13: In some examples of the catheter of clause 1, wherein at least one of the first coil member or the second coil member includes a cut hypotube.

Clause 14: In some examples of the catheter of clause 1, wherein at least one of the first coil member or the second coil member includes a round-wire.

Clause 15: In some examples of the catheter of clause 1, wherein the first and second coil members are formed from materials having different elasticities.

Clause 16: In some examples of the catheter of clause 1, wherein at least one of the first coil member or the second coil member includes a metal.

Clause 17: In some examples of the catheter of clause 16, wherein the metal includes at least one of a nickel titanium alloy, stainless steel, tungsten, titanium, gold, platinum, palladium, tantalum, silver, cobalt-chromium alloy, or a nickel-chromium alloy.

Clause 18: In some examples of the catheter of clause 1, wherein at least one of the first coil member or the second coil member includes a cladded wire.

Clause 19: In some examples of the catheter of clause 1, wherein at least one of the first coil member or the second coil member includes a synthetic fiber.

Clause 20: In some examples of the catheter of clause 19, wherein the synthetic fiber includes at least one of a para-aramid material, liquid crystal polymer, poly(p-phenylene-2,6-benzobisoxazole), ultra-high molecular weight polyethylene, polyethylene naphthalate, polyester, carbon fiber a glass-fiber reinforced polymer, or a carbon-fiber reinforced polymer Clause 21: In some examples of the catheter of clause 1, wherein at least one of the first coil member or the second coil member includes a polymer.

Clause 22: In some examples of the catheter of clause 21, wherein the polymer includes at least one of polycarbonate, polyimide, polyetherimide, polyphenylene sulfide, or polyether-ether-ketone.

Clause 23: In some examples of the catheter of clause 1, wherein at least one of the first coil member or the second coil member includes a fluoropolymer.

Clause 24: In some examples of the catheter of clause 23, wherein the fluoropolymer includes at least one of polytetrafluoroethylene, poly(ethene-co-tetrafluoroethene), fluorinated ethylene propylene, or polyvinylidene fluoride.

Clause 25: In some examples of the catheter of clause 1, wherein at least one of the first coil member or the second coil member includes a thermoplastic polymer.

Clause 26: In some examples of the catheter of clause 25, wherein the thermoplastic polymer includes at least one of a polyether block amide, a polyamide, a polyurethane, a polyolefin, or a thermoplastic elastomer.

Clause 27: In some examples of the catheter of clause 1, wherein at least one of the first coil member or the second coil member includes a thermoset polymer.

Clause 28: In some examples of the catheter of clause 1, wherein at least one of the first coil member or the second coil member is formed from a material having a lower durometer than the outer jacket.

Clause 29: In some examples of the catheter of clause 1, wherein the outer jacket and the first coil member are formed from a same material.

Clause 30: In some examples of the catheter of clause 1, wherein the first coil member is more radiopaque than the second coil member.

Clause 31: In some examples of the catheter of clause 1, further including an inner liner defining an inner lumen of the elongated body, the first and second coil members being positioned between the inner liner and the outer jacket.

Clause 32: In some examples of the catheter of clause 31, wherein the first and second coil members are each directly adjacent to the inner liner.

Clause 33: In some examples of the catheter of clause 1, wherein the first and second coil members do not cross or overlap each other.

Clause 34: In some examples of the catheter of clause 1, wherein all coil members of the elongated body are wound in the same direction.

Clause 35: In one example a catheter including an elongated body including a structural support layer including at least two filaments of different materials wound longitudinally adjacent to each other to define a coil structure; and an outer jacket positioned over the structural support layer.

Clause 36: In some examples of the catheter of clause 35, wherein the at least two filaments includes a first filament and a second filament formed of a different material than the first filament, the coil structure including alternating turns of the first and second filaments.

Clause 37: In some examples of the catheter of clause 35, wherein the at least two filaments includes a first filament and a second filament formed of a different material than the first filament, the coil structure including more turns of the first filament than the second filament.

Clause 38: In some examples of the catheter of clause 35, wherein the at least two filaments includes a plurality of first filaments and at least one second filament formed of a different material than the first filaments.

Clause 39: In some examples of the catheter of clause 35, further including an inner liner defining an inner lumen of the elongated body, the at least two filaments being wound around the inner liner and positioned between the inner liner and the outer jacket.

Clause 40: In some examples of the catheter of clause 35, wherein at least one turn of the second filament is positioned between adjacent turns of the first filament.

Clause 41: In some examples of the catheter of clause 35, wherein the first filament contacts the second filament.

Clause 42: In some examples of the catheter of clause 35, wherein turns of the first filament and turns of the second filament are longitudinally offset from each other.

Clause 43: In some examples of the catheter of clause 42, wherein the offset defines a first gap distance along a proximal portion of the elongated body and a second gap distance along a distal portion of the elongated body, the second gap distance being different than the first gap distance.

Clause 44: In some examples of the catheter of clause 43, wherein the first gap distance is less than the second gap distance.

Clause 45: In some examples of the catheter of clause 35, wherein the first filament and the second filament are wound in a same direction.

Clause 46: In some examples of the catheter of clause 35, wherein the first filament and the second filament have substantially same pitches.

Clause 47: In some examples of the catheter of clause 35, wherein the first and second filaments have different pitches.

Clause 48: In some examples of the catheter of clause 35, wherein the catheter includes a plurality of filaments, the plurality including the first and second filaments, and further including at least one additional filament formed from a same material as the first filament.

Clause 49: In some examples of the catheter of clause 35, wherein the second filament is interspaced with only a portion of the first filament.

Clause 50: In some examples of the catheter of clause 35, wherein at least one of the first filament or the second filament includes a flat-wire.

Clause 51: In some examples of the catheter of clause 35, wherein at least one of the first filament or the second filament includes a cut hypotube.

Clause 52: In some examples of the catheter of clause 35, wherein at least one of the first filament or the second filament includes a round-wire.

Clause 53: In some examples of the catheter of clause 35, wherein the first and second filaments are formed from materials having different elasticities.

Clause 54: In some examples of the catheter of clause 35, wherein at least one of the first filament or the second filament includes a metal.

Clause 55: In some examples of the catheter of clause 54, wherein the metal includes at least one of a nickel titanium alloy, stainless steel, tungsten, titanium, gold, platinum, palladium, tantalum, silver, cobalt-chromium alloy, or a nickel-chromium alloy.

Clause 56: In some examples of the catheter of clause 35, wherein at least one of the first filament or the second filament includes a cladded wire.

Clause 57: In some examples of the catheter of clause 35, wherein at least one of the first filament or the second filament includes a synthetic fiber.

Clause 58: In some examples of the catheter of clause 57, wherein the synthetic fiber includes at least one of a para-aramid material, liquid crystal polymer, poly(p-phenylene-2,6-benzobisoxazole), ultra-high molecular weight polyethylene, polyethylene naphthalate, polyester, carbon fiber a glass-fiber reinforced polymer, or a carbon-fiber reinforced polymer Clause 59: In some examples of the catheter of clause 35, wherein at least one of the first filament or the second filament includes a polymer.

Clause 60: In some examples of the catheter of clause 59, wherein the polymer includes at least one of polycarbonate, polyimide, polyetherimide, polyphenylene sulfide, or polyether-ether-ketone.

Clause 61: In some examples of the catheter of clause 35, wherein at least one of the first filament or the second filament includes a fluoropolymer.

Clause 62: In some examples of the catheter of clause 35, wherein the fluoropolymer includes at least one of polytetrafluoroethylene, poly(ethene-co-tetrafluoroethene), fluorinated ethylene propylene, or polyvinylidene fluoride.

Clause 63: In some examples of the catheter of clause 35, wherein at least one of the first filament or the second filament includes a thermoplastic polymer.

Clause 64: In some examples of the catheter of clause 63, wherein the thermoplastic polymer includes at least one of a polyether block amide, a polyamide, a polyurethane, a polyolefin, or a thermoplastic elastomer.

Clause 65: In some examples of the catheter of clause 35, wherein at least one of the first filament or the second filament includes a thermoset polymer.

Clause 66: In some examples of the catheter of clause 35, wherein at least one of the first filament or the second filament is formed from a material having a lower durometer than the outer jacket.

Clause 67: In some examples of the catheter of clause 35, wherein the outer jacket and the first filament are formed from a same material.

Clause 68: In some examples of the catheter of clause 35, wherein the first filament is more radiopaque than the second filament.

Clause 69: In some examples of the catheter of clause 35, further including an inner liner defining an inner lumen of the elongated body, the first and second filaments being positioned between the inner liner and the outer jacket.

Clause 70: In some examples of the catheter of clause 69, wherein the first and second filaments are each directly adjacent to the inner liner.

Clause 71: In some examples of the catheter of clause 35, wherein the first and second filaments do not cross or overlap each other.

Clause 72: In some examples of the catheter of clause 35, wherein all filaments of the elongated body are wound in the same direction.

Clause 73: In one example method of forming a catheter, the method including positioning a first coil member over an inner member; positioning a second coil member over the inner member, wherein positioning the second coil member over the mandrel includes interspacing the second coil member with the first coil member, the first and second coil members including different materials; positioning an outer jacket over at least the first coil member.

Clause 74: In some examples of the method of forming a catheter of clause 73, wherein the inner member includes a mandrel.

Clause 75: In some examples of the method of forming a catheter of clause 73, wherein the inner member includes an inner liner.

Clause 76: In some examples of the method of forming a catheter of clause 73, wherein positioning the first and second coil members over the inner member includes winding the first and second coil members over the inner member at different times.

Clause 77: In some examples of the method of forming a catheter of clause 73, wherein positioning the first and second coil members over the inner member includes substantially simultaneously winding the first and second coil members over the inner member.

Clause 78: In some examples of the method of forming a catheter of clause 77, wherein positioning the first and second coil members over the inner member includes positioning the first and second coil members each defining an inner diameter and a respective first coil pitch over the inner member, the inner member having an outer diameter greater than the inner diameter, wherein after the first and second coil members are positioned over the inner member, the first and second coil members each define a second coil pitch greater than the respective first coil pitch.

Clause 79: In some examples of the method of forming a catheter of clause 73, wherein after interspacing the second coil member with the first coil member, at least one turn of the second coil member is positioned between adjacent turns of the first coil member.

Clause 80: In some examples of the method of forming a catheter of clause 73, wherein positioning the second coil member over the inner member includes positioning the second coil member to contact the first coil member.

Clause 81: In some examples of the method of forming a catheter of clause 73, wherein positioning the second coil member over the inner member includes positioning the second coil member to be longitudinally offset from the first coil member.

Clause 82: In some examples of the method of forming a catheter of clause 81, wherein the longitudinal offset defines a first coil spacing along a proximal portion of the elongated body and a second coil spacing along a distal portion of the elongated body, the second coil spacing being different than the first coil spacing.

Clause 83: In some examples of the method of forming a catheter of clause 82, wherein the first coil spacing is less than the second coil spacing.

Clause 84: In some examples of the method of forming a catheter of clause 73, wherein positioning the first and second coil members over the inner member includes winding the first coil member and the second coil member over the inner member in a same direction.

Clause 85: In some examples of the method of forming a catheter of clause 73, wherein the first and second coil members have substantially same pitches.

Clause 86: In some examples of the method of forming a catheter of clause 73, wherein the first and second coil members have different pitches.

Clause 87: In some examples of the method of forming a catheter of clause 73, further including positioning at least one additional coil member over the inner member, the at least one additional coil member formed from a same material as the first coil member.

Clause 88: In some examples of the method of forming a catheter of clause 73, wherein at least one of the first coil member or the second coil member includes a flat-wire.

Clause 89: In some examples of the method of forming a catheter of clause 73, wherein at least one of the first coil member or the second coil member includes a round-wire.

Clause 90: In some examples of the method of forming a catheter of clause 73, wherein at least one of the first coil member or the second coil member includes a cut hypotube.

Clause 91: In some examples of the method of forming a catheter of clause 73, wherein the first and second coil members are formed from materials having different elasticities.

Clause 92: In some examples of the method of forming a catheter of clause 73, wherein at least one of the first coil member or the second coil member includes a metal.

Clause 93: In some examples of the method of forming a catheter of clause 92, wherein the metal includes at least one of a nickel titanium alloy, stainless steel, tungsten, titanium, gold, platinum, palladium, tantalum, silver, cobalt-chromium alloy, or a nickel-chromium alloy.

Clause 94: In some examples of the method of forming a catheter of clause 73, wherein at least one of the first coil member or the second coil member includes a cladded wire.

Clause 95: In some examples of the method of forming a catheter of clause 73, wherein at least one of the first coil member or the second coil member includes a synthetic fiber.

Clause 96: In some examples of the method of forming a catheter of clause 95, wherein the synthetic fiber includes at least one of a para-aramid material, liquid crystal polymer, poly(p-phenylene-2,6-benzobisoxazole), ultra-high molecular weight polyethylene, polyethylene naphthalate, polyester, carbon fiber a glass-fiber reinforced polymer, or a carbon-fiber reinforced polymer Clause 97: In some examples of the method of forming a catheter of clause 73, wherein at least one of the first coil member or the second coil member includes a polymer.

Clause 98: In some examples of the method of forming a catheter of clause 97, wherein the polymer includes at least one of polycarbonate, polyimide, polyetherimide, polyphenylene sulfide, or polyether-ether-ketone.

Clause 99: In some examples of the method of forming a catheter of clause 73, wherein the first material includes a fluoropolymer.

Clause 100: In some examples of the method of forming a catheter of clause 99, wherein the fluoropolymer includes at least one of polytetrafluoroethylene, poly(ethene-co-tetrafluoroethene), fluorinated ethylene propylene, or polyvinylidene fluoride.

Clause 101: In some examples of the method of forming a catheter of clause 73, wherein at least one of the first coil member or the second coil member includes a thermoplastic polymer.

Clause 102: In some examples of the method of forming a catheter of clause 101, wherein the thermoplastic polymer includes at least one of a polyether block amide, a polyamide, a polyurethane, a polyolefin, or a thermoplastic elastomer.

Clause 103: In some examples of the method of forming a catheter of clause 73, wherein at least one of the first coil member or the second coil member includes a thermoset polymer.

Clause 104: In some examples of the method of forming a catheter of clause 73, wherein at least one of the first coil member or the second coil member is formed from a material having a lower durometer than the outer jacket.

Clause 105: In some examples of the method of forming a catheter of clause 73, wherein the outer jacket and the first coil member are formed from a same material.

Clause 106: In some examples of the method of forming a catheter of clause 73, wherein the first coil member is more radiopaque than the second coil member.

Clause 107: In some examples of the method of forming a catheter of clause 73, wherein positioning the outer jacket includes positioning the outer jacket over the first and second coil members.

Clause 108: In some examples of the method of forming a catheter of clause 73, further including, after positioning the outer jacket over the first and second coil members, applying heat to cause a material from which the second coil member is formed to reflow and bond to the outer jacket.

Clause 109: In some examples of the method of forming a catheter of clause 73, further including removing at least a portion of the second coil member before positioning the outer jacket over at least the first coil member.

Clause 110: In some examples of the method of forming a catheter of clause 109, wherein removing the at least the portion of the second coil member includes etching the at least the portion of the second coil member.

Clause 111: In some examples of the method of forming a catheter of clause 109, wherein removing the at least the portion of the second coil member includes dissolving the at least the portion of the second coil member.

Clause 112: In some examples of the method of forming a catheter of clause 109, wherein removing the at least the portion of the second coil member includes removing a portion of the second coil member interspaced with a proximal section of the first coil member.

Clause 113: In some examples of the method of forming a catheter of clause 109, wherein removing the at least the portion of the second coil member includes removing the entire second coil member.

Clause 114: In one example a method including introducing an elongated body into a patient, the elongated body including a first coil member; a second coil member interspaced with the first coil member, the first and second coil members including different materials; and an outer jacket positioned over the first and second coil members; and guiding the distal end of the elongated body to a treatment site within the patient.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

An example medical catheter ("catheter") described herein includes a relatively flexible catheter body (e.g., elongated body) that can be configured to be navigated through vasculature of a patient, e.g., tortuous vasculature in a brain of the patient. The catheter body can be configured to exhibit a relatively high level of flexibility, pushability, torqueability, and/or structural integrity.

In some examples, the catheter body includes an inner liner, a plurality of filaments (e.g. coil members) in a support layer, and an outer jacket, which can interact to provide a relatively flexible catheter body with sufficient structural integrity (e.g., columnar strength) to permit the catheter body to be advanced through the vasculature via a pushing force applied to a proximal portion of the catheter body, e.g. without buckling, kinking, or otherwise undesirably deforming (e.g., ovalization). In some examples, the flexible catheter body is configured to substantially conform to the curvature of the vasculature. In addition, in some examples, the catheter body has a columnar strength and flexibility that allow at least a distal portion of the catheter body to be navigated from a femoral artery, through the aorta of the patient, and into the intracranial vascular system of the patient, e.g., to reach a relatively distal treatment site, including the middle cerebral artery (MCA), the Circle of Willis, and tissue sites more distal than the MCA and the Circle of Willis. The MCA and, consequently, vasculature distal to the MCA may be relatively difficult to access due to the carotid siphon or vertebral artery anatomy that must be traversed to reach such locations.

Although primarily described as being used to reach relatively distal vasculature sites, the multi-filament catheters described herein may readily be configured to be used with other target tissue sites. For example, the catheters may be used to access tissue sites throughout the coronary and peripheral vasculature, the gastrointestinal tract, the urethra, ureters, fallopian tubes and other body lumens of a patient.

Figure 1:
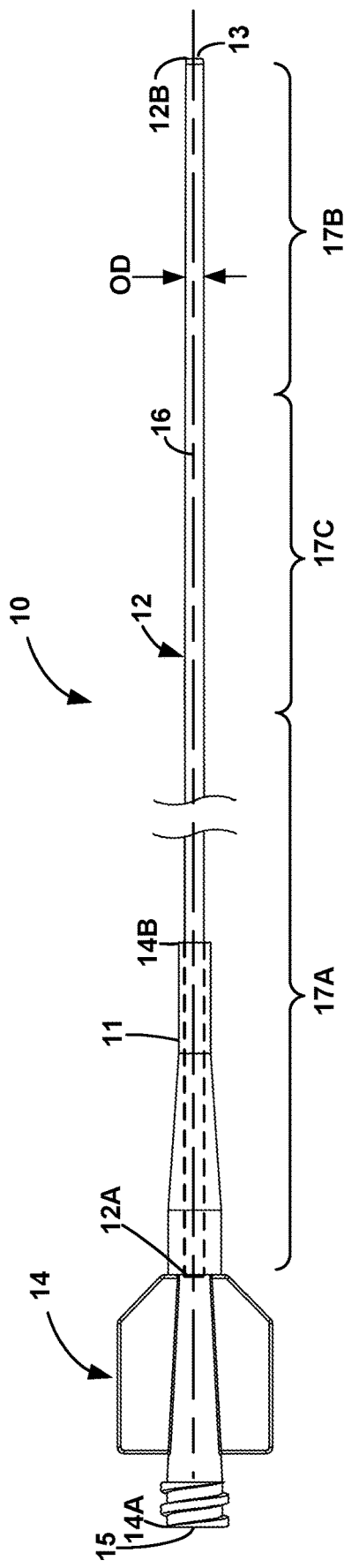
FIG. 1 is a conceptual side elevation view of an example catheter, which includes an elongated body and a hub.

FIG. 1 is a conceptual side view of an example catheter 10, which includes elongated body 12 and a hub 14 positioned at a proximal end 12A of elongated body 12. Elongated body 12 may extend from proximal end 12A to distal end 12B, and defines a proximal portion 17A, medial portion 17C, and distal portion 17B. Elongated body 12 may define at least one inner lumen 26 (shown in FIG. 2) that extends the length of elongated body 12. In the example shown in FIG. 1, proximal end 12A of elongated body 12 is received within hub 14 and can be mechanically connected to hub 14 via an adhesive, welding, or another suitable technique or combination of techniques. Opening 15 defined by hub 14 and located at proximal end 14A of hub 14 is aligned with the inner lumen 26 (shown in FIG. 2) of elongated body 12, such that the inner lumen 26 of elongated body 12 may be accessed via opening 15. In some examples, catheter 10 may include a strain relief body 11, which may be a part of hub 14 or may be separate from hub 14.

In other examples, the proximal end of catheter 10 can include another structure in addition to or instead of hub 14. In some examples, catheter hub 14 may define an opening through which an inner lumen 26 (shown in FIG. 2) of elongated body 12 may be accessed and, in some examples, closed. For example, catheter hub 14 may include one or more luers or other mechanisms for establishing connections between catheter 10 and other devices.

In some cases, a clinician may steer catheter 10 through the vasculature of a patient by pushing or rotating hub 14 to introduce distal portion 17B of elongated body 12 through the vasculature of a patient. The clinician may apply torque to hub 14 and/or proximal portion 17A of the catheter 10 (or at least a portion of elongated body 12 that is more proximal than distal portion 17B implanted in the patient) in order to rotate distal portion 17B of catheter 10. As described further below, in some examples, elongated body 12 includes a plurality of coiled filaments, which may configure elongated body 12 to better transmit the torque applied to a relatively proximal portion to a relatively distal portion of elongated body 12 compared to some single filament coil or braided filament catheters. Elongated body 12 may be relatively resistant to kinking or otherwise undesirably deforming upon rotation of catheter 10 and/or exhibit a high degree of responsiveness from the relatively proximal portion 17A of elongated body 12. For example, the elongated body 12 may include a plurality of filaments (e.g., two or more helical coil members) wound around an inner liner or otherwise defining respective coil members that are adjacent to each other in the longitudinal direction. The adjacent turns of the filaments may be longitudinally offset from one another along elongated body 12, which are configured to help distribute the torsional forces along elongated body 12.

In some examples, catheter 10 may be a guide catheter that acts as a conduit to help support a microcatheter. In other examples, catheter 10 may be a microcatheter. In either example, elongated body 12 of catheter 10 may define an inner lumen (e.g., inner lumen 26 of FIG. 2), which may be configured to receive one or more medical devices, deliver a therapeutic agent to a distal tissue site, remove thrombus (e.g., by aspiration) from the patient's vasculature, and the like or any combination thereof. Example therapeutic agents include, but are not limited to, an oxygenated medium or a pharmaceutical agent, which may be, for example, a vasodilator such as nifedipine or sodium nitroprusside, or a tissue plasminogen activator (t-PA), which can be used to breakdown blood clots. In examples in which the inner lumen defined by elongated body 12 is used to remove thrombus from vasculature, catheter 10 may be referred to as an aspiration catheter. A vacuum may be applied to a proximal end of catheter 10 (e.g., opening 15) to draw a thrombus into the inner lumen. An aspiration catheter may be used in a medical procedure to treat an ischemic insult, which may occur due to occlusion of a blood vessel that deprives brain tissue of oxygen-carrying blood. In some examples, in addition to being configured to be navigated to relatively distal tissue sites, an aspiration catheter may also include a distal tip configuration that is configured to substantially maintain its shape, even in the presence of the vacuum force applied to the catheter during the aspiration process.

In some examples, catheter 10 may be advanced to a target location within vasculature of the patient in cooperation with a guidemember (not shown) such as a guidewire, an inner catheter, both a guidewire and an inner catheter, or the like, which may aid in the navigation (e.g., steering and manipulation) of elongated body 12 through the vasculature. For example, at least part of an inner lumen of elongated body 12 may be configured to receive a guidemember or an inner catheter, such that the catheter body may be guided through vasculature over the guidemember or the inner catheter. In some examples, this distal tip of elongated body 12 (e.g., the region defined by distal opening 13) may be configured to resist geometric deformation (e.g., kinking, ovalization, or the like) from forces applied to the distal tip by the guidewire or inner catheter. This resistance to geometric deformation may help improve the ease with which elongated body 12 may be guided to a relatively distal tissue site, e.g., through relatively tight turns in the vasculature and/or the responsiveness of catheter 10 as a clinician guides the distal tip of elongated body 12 through the vasculature of a patient.

In some examples, elongated body 12 may be used to access relatively distal vasculature locations in a patient, such as the MCA in a brain of a patient. The MCA, as well as other vasculature in the brain or other relatively distal tissue sites (e.g., relative to the vasculature access point), may be relatively difficult to reach with a catheter, due at least in part to the tortuous pathway (e.g., comprising relatively sharp twists and/or turns) through the vasculature to reach these tissue sites.

Elongated body 12 that includes a plurality of adjacent coil members may be structurally configured to be relatively flexible, pushable, navigable, and relatively kink- and buckle-resistant, so that it may resist buckling when a pushing force is applied to a relatively proximal portion of catheter 10 to advance elongated body 12 distally through vasculature, and so that it may resist kinking when traversing around a tight turn in the vasculature. Unwanted kinking and/or buckling of elongated body 12 may otherwise hinder a clinician's efforts to push the elongated body 12 distally, e.g., past a turn. For example, placing the coil members 18 and 20 longitudinally adjacent to each other may help avoid an abrupt stiffness transition compared to other catheters comprising overlapping braided filaments. In some examples, the plurality of coil members placed longitudinally adjacent to each other may exhibit better columnar strength (e.g., kink resistance) and/or hoop strength (e.g., resistance to ovalization) compared to a catheter having only a single filament coil or braid filaments.

In some examples, elongated body 12 may define an outer diameter taper (e.g., gradient, gradation, segmented gradient or gradation, or the like) along its working length of elongated body 12. The outer diameter of elongated body is labeled "OD" in FIG. 1. The outer diameter taper may assist with the navigability and/or maneuverability of elongated body 12 through the vasculature of a patient. In some examples, the outer diameter taper may define a continuous transition gradient from an outer diameter of elongated body 12 defined at hub distal end 14B the outer diameter at distal end 12B of elongated body 12. In other examples, the outer diameter of elongated body 12 may define a discontinuous transition (e.g., a gradation or discrete step-downs) in outer diameter to define the outer diameter taper. The size of each discontinuous transition (e.g., each discrete step-downs) in the outer diameter may be selected to reduce the number of edges/ridges on the outer surface of elongated body 12 that may potentially catch on anatomical features within the vasculature as elongated body 12 is advanced through vasculature.

In some examples, at least a part (e.g., only part of the working length or the entire working length) of elongated body 12 may define a constant outer diameter. In such examples, the plurality of filaments of elongated body 12 discussed further below may be configured to provide sufficient support to elongated body 12 to allow the outer diameter of the elongate body 12 to remain relatively small along the length of elongated body 12 to facilitate distal flexibility about distal portion 17B while still retaining sufficient strength an pushability about proximal portion 17A. Additionally or alternatively, a relatively small outer diameter of elongated body 12 may allow for easier to navigability of the catheter 10 through tortuous vasculature of a patient. Thus, by maintaining a relatively small outer diameter of elongated body 12 at distal portion 17B, which leads elongated body 12 through vasculature, elongated body 12 may better traverse through tortuous vasculature with still maintaining a relatively high level of proximal pushability due to the support structures.

In some examples, proximal portion 17A of elongated body 12 may define a relatively large outer diameter to provide better proximal support for elongated body 12, which may help increase the navigability and maneuverability of elongated body 12 through the vasculature of a patient. In some cases, proximal portion 17A may not be introduced into low profile or tortuous arteries, such that the cross-sectional size of proximal portion 17A may be increased in favor of proximal support without adversely affecting the ability of elongated body 12 to reach relatively distal tissue sites.

In some examples, the outer diameter of elongated body 12 may taper from about 6 French (e.g., 6 French or nearly 6 French) at proximal end 12A to about 5 French (e.g., 5 French or nearly 5 French) at the distal portion 17B. In other examples, the outer diameter of elongated body 12 may taper from about 4 French (e.g., 4 French or nearly 4 French) at proximal end 12A to about 5 French (e.g., 3 French or nearly 3 French) at the distal portion 17B. In other examples, the outer diameter of elongated body 12 may remain substantially constant (e.g., constant or nearly constant) in the range of about 3 French and about 6 French. In some examples, the outer diameter of elongated body 12 may be larger than 6 French, for example 8 French. The measurement term French, abbreviated Fr or F, is three times the diameter of a device as measured in millimeters (mm). Thus, an 8 French diameter is about 2.67 mm, a 6 French diameter is about 2 mm, a 5 French diameter is about 1.67 mm, a 4 French diameter is about 1.33 mm, and a 3 French diameter is about 1 mm. In some examples, the outer diameter of elongated body 12 may be between about 1 mm to about 2.67 mm.

The proximal, distal, and medial portions 17A-17C of elongated body 12 may each have any suitable length for accessing a target tissue site within the patient from a vasculature access point. The length may be measured along longitudinal axis 16 of elongated body 12. In some examples, the length of proximal portion 17A that extends from distal end 14B of hub 14 to medial portion 17C may be about 38.16 inches (about 96.93 cm), medial portion 17C may have a length of about 1 inch (about 2.5 cm) to about 3 inches (about 7.6 cm), such as about 2 inches (about 5 cm) and distal portion 17B has a length of about 11.1 inches (about 30 cm). However, in other examples, proximal, distal, and medial portions 17A-17C may have different lengths.

In some examples the working length of elongated body 12 may be measured from hub distal end 14B of hub 14 (marked by the distal end of optional strain relief body 11) to distal end 12B of distal portion 17B. The working length of catheter 10 may depend on the location of the target tissue and/or the medical procedure for which catheter 10 is used. For example, if catheter 10 is a distal access catheter used to access vasculature in a brain of a patient from a femoral artery access point at the groin of the patient, catheter 10 may have a working length of about 129 centimeters (cm) to about 135 cm, such as about 132 cm, although other lengths may be used. In other examples, or for other applications, the working length of elongated body 12 may have different lengths.

In some examples, the diameter of inner lumen 26 ("ID" of FIG. 2) of elongated body 12, also referred to herein as an inner diameter of elongated body 12, may be substantially constant from proximal end 12A to distal end 12B. In other examples, the inner diameter of elongated body 12 may taper from a first inner diameter at a proximal portion that includes proximal end 12A to a second inner diameter at a distal portion that includes distal end 12B, the second inner diameter being smaller than the first inner diameter. For example, an inner diameter of elongated body 12 may taper from a first inner diameter of about 0.0685 inches (about 1.74 mm) to a second inner diameter of about to 0.0605 inches (about 1.54 mm). The inner diameter may, for example, gradually taper along the portion of inner lumen 26 extending through medial portion 17C of elongated body 12, where the taper can be linear, curved, continuous or discontinuous; e.g., the inner diameter of elongated body 12 may step-down from the first inner diameter to the second inner diameter in discrete steps.

In some examples, elongated body 12 can be relatively thin-walled, such that it defines a relatively large inner diameter (ID) for a given outer diameter (OD), which may further contribute to the flexibility and maneuverability of elongated body 12. The wall thickness ("T" of FIG. 2) of elongated body 12 may be half the difference between the outer diameter of elongated body 12 and the inner diameter of elongated body 12, as defined by inner lumen 26.

Figure 2:
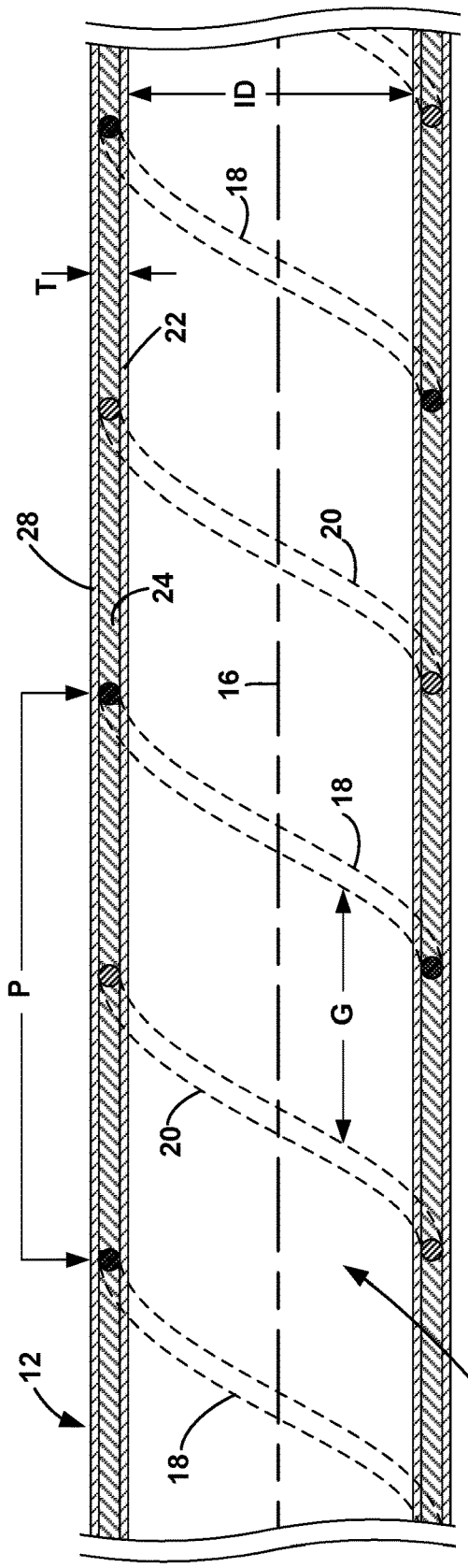
FIG. 2 is a conceptual axial cross-sectional view of a part of the elongated body of FIG. 1, where the cross-section is taken through a center of the elongated body along a longitudinal axis.

FIG. 2 is a conceptual axial cross-sectional view of a part of elongated body 12 of FIG. 1 (e.g., medial portion 17C), where the cross-section is taken through a center of the elongated body along a longitudinal axis 16. As shown in FIG. 2, elongated body 12 includes an inner liner 22, a plurality of filaments (e.g. first and second coil members 18 and 20) in a support layer 24, and outer jacket 28.

Inner liner 22 defines inner lumen 26 of elongated body 12, inner lumen 26 extending from proximal end 12A to distal end 12B and defining a passageway extending from proximal end 12A to distal opening 13 at distal end 12B of elongated body 12. In other examples, however, elongated body 12 may be a linerless body and may not include inner liner 22; rather, inner lumen 26 of elongated body 12 may be defined, at least in part, by support layer 24. Inner lumen 26 may be sized to receive a medical device (e.g., another catheter, a guidewire, an embolic protection device, a stent, a thrombectomy device, or any combination thereof), a therapeutic agent, or the like. At least the inner surface of inner liner 22 defining inner lumen 26 may be lubricious in some examples in order to facilitate the introduction and passage of a device, a therapeutic agent, or the like, through inner lumen 26. For example, the material from which the entire inner liner 22 is formed may be lubricious. In other examples, inner liner 22 may be formed from two or more materials, where the material that defines inner lumen 26 may be more lubricious than the material that interfaces with structural support coils 18 and 20 and support layer 24. In some examples, the inner liner 22 may be coated with a lubricious coating after the liner is formed.

Example materials from which inner liner 22 may be formed include, but are not limited to, polytetrafluoroethylene (PTFE), fluoropolymer, perfluoroalkyoxy alkane (PFA), fluorinated ethylene propylene (FEP), or any combination thereof. For example, inner liner 22 may be formed from a non-etched PTFE, e.g., may consist essentially of a non-etched PTFE. In other examples, the liner may be made of a lubricious polyolefin material.

In some examples, inner liner 22 is a single, seamless tubular body, such that inner lumen 26 of elongated body 12 is continuous along its entire length, e.g., from proximal end 12A to distal opening 13. A seamless inner liner 22 may, for example, be devoid of any seams (e.g., the seam formed from joining two separate tubular bodies together at an axial location along longitudinal axis 16), such that the seamless inner liner 22 is a unitary body, rather than multiple, discrete bodies that are separately formed and subsequently connected together. In addition, in some examples, inner liner 22 defines a substantially constant (e.g., constant or nearly constant) inner diameter ("ID" of FIG. 2) along the entire length of inner liner 22, while in other examples, inner liner 22 may define different inner diameters along longitudinal axis 16. For example, inner liner 22 may define a first inner diameter along a proximal portion of inner liner 22 (e.g., along proximal portion 17A) and a second inner diameter along a distal portion of inner liner (e.g., along distal portion 17B), the second inner diameter being smaller than the first inner diameter. For example, inner liner 22 may taper continuously from the first inner diameter to the second inner diameter, or may define one or more step-downs in inner diameter along the length of inner liner 22.

A seamless inner liner 22 may be easier to slide over another device, e.g., another catheter or a guidemember, compared to a catheter formed from two or more longitudinal sections that are mechanically connected to each other because the seamless inner liner may define a smoother inner lumen 26. In contrast, joints between sections of an inner liner that are formed from two or more longitudinal sections may define surface protrusions or other irregularities along inner lumen 26 which may interfere with the passage of devices through inner lumen 26. In addition, a seamless inner liner 22 may help distribute pushing and rotational forces along the length of elongated body 12. Thus, the seamless inner liner 22 may help contribute to the pushability of elongated body 12.

In some examples in which inner liner 22 defines inner lumen 26 having different diameters, the wall thickness ("T" in FIG. 2) of elongated body 12 may vary along the length of elongated body 12. For example, the wall thickness T in proximal portion 17A may be greater than wall thickness (T) in distal portion 17B. In other examples, the wall thickness (T) may be substantially constant (e.g., constant or nearly constant) along a length of elongated body 12.

Support layer 24 of elongated body 12 may include a plurality filaments, for example, first coil member 18 and a second coil member 20 (also collectively referred to as "coil members"). Coil members 18 and 20 may each define a plurality of turns in the shape of a helical coil, each coil member defining a central axis substantially aligned with longitudinal axis 16. First coil member 18 and second coil member 20 may be interspaced with each other in a longitudinal direction (in a direction along longitudinal axis 16) such that the helical coils are wound in the same direction (e.g., a right-handed wind) with one turn (e.g., one full circumvolution about liner 22) of the second coil member 20 positioned between an adjacent turn of the first coil member 18 so that the turns of coil members 18 and 20 are longitudinally offset from one another along the length of elongated body 12. In some examples, coil members 18 and 20 may be wound such that the coil members do not overlap along the length of elongated body 12. As discussed further below, in some examples, the interspaced arrangement of the plurality of coil members 18 and 20 may allow for improved rotational responsiveness and structural integrity compared to filament catheters including a single-filament coil or a braided-filament.

Structural characteristics of coil members 18 and 20 may be tailored to increase the structural integrity of elongated body 12 while allowing elongated body 12 to remain relatively flexible. For example, coil members 18 and 20, together with inner liner 22, support layer 24, and outer jacket 28, may help distribute pushing and rotational forces along a length of elongated body 12, while also providing structural support to help prevent kinking or buckling of elongated body 12 upon bending or rotation of elongated body 12. As a result, a clinician may apply pushing forces, rotational forces, or both, to a proximal portion of elongated body 12, and such forces may cause a distal portion of elongated body 12 to advance distally, rotate, or both, respectively.

The structural characteristics of coil members 18 and 20 may include, for example, the materials from which members 18 and 20 are formed, the dimensions of the filament (e.g., a wire) used to form coil members 18 and 20, the type of filament (e.g., a flat wire or a round wire) used to form coil members 18 and 20, the coil spacings defined by coil members 18 and 20, the pitch of coil members 18 and 20, and the like. In some examples, coil members 18 and 20 may be formed from materials selected to provide certain structural characteristics. For example, coil members 18 and 20 may include one or more coil members that include shape memory materials (e.g., metals) configured to help elongated body 12 substantially maintain its cross-sectional shape or at least help prevent elongated body 12 from buckling or kinking as it is navigated through tortuous vasculature of a patient. In some examples, one or more coil members 18 and 20 may include materials configured to increase the flexibility of elongated body 12 to improve the navigability of elongated body 12 through the vasculature of a patient.

Suitable materials for coil members 18 and 20 may include, for example, one or more metals such as nickel titanium alloy (e.g., Nitinol, tertiary Nitinols), stainless steel, tungsten, titanium, gold, platinum, palladium, tantalum, silver, or a nickel-chromium alloy, a cobalt-chromium alloy, or the like.

In some examples, one or more coil members 18 and 20 may include one or more synthetic fibers including, for example, at least one of a para-aramid material, liquid crystal polymer (LCP), poly(p-phenylene-2,6-benzobisoxazole), polyether amides, polycarbonates, PTFE, PEEK, ultra-high molecular weight polyethylene, polyethylene naphthalate, polyester, carbon fiber a glass-fiber reinforced polymer, a carbon-fiber reinforced polymer, or the like.

In some examples, one or more coil members 18 and 20 may include one or more polymers including, for example, polycarbonate, polyimide, polyetherimide, polyphenylene sulfide, polyether-ether-ketone, one or more fluoropolymers such as polytetrafluoroethylene, poly(ethene-co-tetrafluoroethene), fluorinated ethylene propylene, polyvinylidene fluoride, or the like, one or more thermoplastic polymers such as polyether block amide, a polyamide, a polyamide-based polymer (e.g., nylon), a polyurethane, a polyolefin, PEBAX, polypropylene, a thermoplastic elastomer, or the like, one or more thermoset polymers, or the like. In some examples, one or more coil members 18 and 20 may include substantially hard and/or rigid based polymer materials including, for example, Kevlar, LCP, nylon, ultra high molecular weight polyethylene, FPEN, polyester, glass-fiber reinforced or carbon-fiber reinforced polymers, or the like that may be used to provide columnar and or hoop strength to elongated body 12. In some examples, forming one or more coil members 18 and 20 using a thermoplastic polymer may help improve the flexibility of the elongated body 12. Additionally or alternatively, including at least one coil member made of a thermoplastic polymer may help fill and/or eliminate any voids in the support layer 24 between other adjacent coil members (e.g., stainless steel wires) by, for example, being reformed through subsequent heat processing.

In some examples, one or more coil members 18 and 20 may be selected to include a radiopaque material to allow elongated body 12 to be easily observed by the clinician as catheter 10 is advanced through the vasculature of a patient. In some examples, first coil member 18 may be formed from materials that have a different elasticity compared to second coil member 20.

In some examples the coil members may be cladded with one or more materials, for example, to improve the radiopacity of the coil material without altering the underlying structural characteristics of the coil material (e.g., Nitinol wire cladded in gold), provide a dissolvable/reflowable spacer material (e.g., polymer) that may be used to help set the pitch and gap spacing between the coil members that is then subsequently removed or reformed as support layer 24, to provide a boding material to the underlying coil member to improve adhesion of the coil member to inner liner 22 and/or outer jacket 28.

In some examples, coil members 18 and 20 may be respectively formed from one or more wire filaments. In some examples, coil members 18 and 20 may include a rounded filaments (e.g., round-wires), half-round filaments, flat-wound filaments (e.g., flat-wires), or the like. A round-wire may define a coil member having a smaller surface area than a flat wire, such that, for a given length of coil members 18 and 20, the rounded wire may be more tightly wound compared to a flat wire. Because the tightness with which the wire is wound to define the coil member may affect the stiffness of the coil member, the rounded coil member may allow for the formation of a coil member 18 and 20 having a larger range of stiffness than then a flat wire. In this way, a rounded wire may, in some examples, achieve a coil member having a more flexible distal portion and a stiffer proximal portion than a comparatively wound flat wire.

In some examples, coil members 18 and 20 may be an etched or cut hypotube such as a spirally cut hypotube. In such examples, the hypotube may define a smaller diameter compared to inner liner 22. The hypotube may be radially expanded (e.g., partially uncoiled) to fit over inner liner 22. By radially expanding the hypotube, the pitch of the hypotube (discussed below) may be increased to define an interspaced gap between turns of the hypotube for receiving one or more additional coil members.

First coil member 18 and second coil member 20 may be made with different materials than each other. For example, first coil member 18 may include Nitinol and second coil member 20 may include stainless steel. In such examples, the stainless steel coil member may provide increased strength to elongated body 12 (e.g., to increase the resistance of elongated body 12 to kinking), whereas the Nitinol coil may provide increased elasticity and flexibility to elongated body 12. Thus, the combination of Nitinol & stainless steel may provide elongated body 12 with the desired kink resistance and flexibility attributes. Further, by interspacing coil members 18 and 20 with each other, abrupt changes in the stiffness of elongated body 12 may be minimized or even avoided. In other examples, first coil member 18 and second coil member 20 may be made from different types of materials (e.g., first coil member 18 is metal based while second coil member 20 is polymer based).

In addition to the type of material used to form coil members 18 and 20, in some examples, the geometry characteristics of the filaments may be selected to tailor the structural characteristics of elongated body 12 to the desired application of catheter 10. Coil members 18 and 20 may define a respective pitch ("P" of FIG. 2) representing the axial distance along longitudinal axis 16 for a respective coil member to complete one full turn around longitudinal axis 16 or around liner 22). In some examples, each coil member 18 and 20 may define a pitch (P) that may be of about 0.004 inches to about 0.13 inches (e.g., about 0.01 cm to about 0.33 cm). In some examples, the pitch (P) may be about 0.0385 inches (e.g., about 0.0978 cm), about 0.0365 inches (e.g., about 0.0927 cm), about 0.0625 inches (e.g., about 0.159 cm), about 0.068 inches (e.g., about 0.173 cm), about 0.100 inches (e.g., about 0.254 cm), or about 0.131 inches (e.g., about 0.333 cm). In some examples, a pitch of coil members 18 and 20 varies along a length of coil members 18 and 20, such that a stiffness (or flexibility) varies along the length. The pitch may continuously vary along the length of member 20, or may progressively change, e.g., include different sections, each section having a respective pitch. In some examples, the pitch (P) of the respective coil members 18 and 20 may be substantially the same (e.g., the same or nearly the same pitch) within respective portions of elongated body 12. For example, coil members 18 and 20 may define a first pitch that is substantially the same (e.g., the same or nearly the same pitch) within proximal portion 17A and define a second pitch that is substantially the same (e.g., the same or nearly the same pitch) within distal portion 17B that is different than the first pitch.

Coil members 18 and 20 may also define one or more coil spacings ("G" of FIG. 2, also referred to as gap distance), which represents the interspatial distance between adjacent turns of adjacent portions of coil members 18 and 20, as measured along longitudinal axis 16. The coil spacing (G) between each coil member 18 and 20 may depend on the number of coil members present and the pitch (P) of each coil member (e.g., a greater number of coils and/or a shorter pitch (P) may decrease the coil spacing (G)). In some examples, the coil spacing (G) may be between about 0 inches to about 0.027 inches (e.g., about 0.069 cm). In examples in which the coil spacing (G) between coil member 18 and 20 is 0 cm, the coil members may be in direct contact with one another.

The pitch (P) of each coil and the coil spacing (G) between the adjacent turns may depend on a variety of geometric factors including, for example, the filament width/diameter of a respective coil, the outer diameter of liner 22, and/or the total number of coil members/filaments included in support layer 24. In some examples, coils members 18 and 20 may define a substantially constant (e.g., constant or nearly constant) pitch (P) and coil spacing (G). Such examples may allow for substantially consistent (e.g. consistent or nearly consistent) structural characteristics along the length of elongated body 12.

Figure 3A:
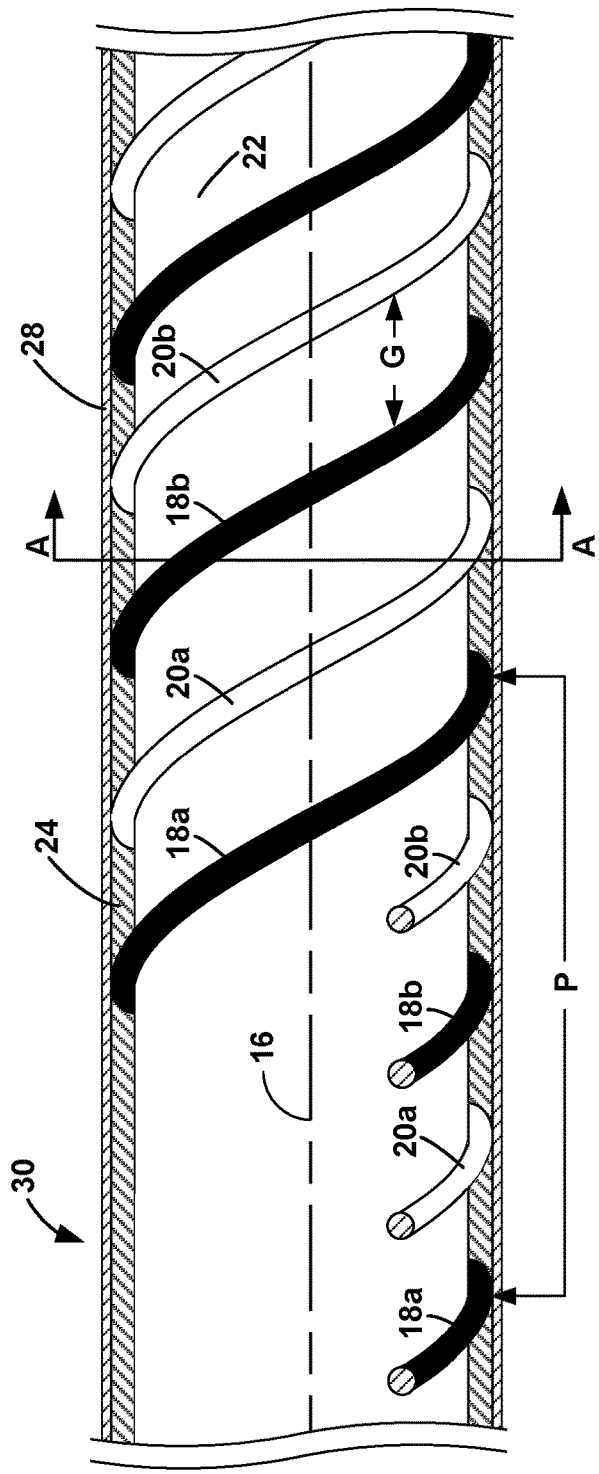
FIG. 3A is a conceptual axial cross-sectional view of an example elongated body that includes four coil members.

In some examples, adjusting the pitch (P), coil spacing (G), and/or the number coil members 18 and 20 of elongated body 12 may affect the structural characteristics of catheter 10. For example, increasing the number of filaments (e.g., coil members) or shortening the pitch of the filaments will increase the amount of filament material present in the radial cross-section of elongated by 12 as described with respect to FIGS. 3A and 3B. FIG. 3A shows a conceptual axial cross-sectional view of an example elongated body 30 that includes four coil members 18a, 18b, 20a, and 20b wrapped around inner liner 22. Coil members 18a, 18b, 20a, and 20b are illustrated in an alternating pattern (e.g., coil member 18a followed by coil member 20a, followed by coil member 18b, followed by coil member 20b). In some examples, two or more of coil members 18a, 18b, 20a, and 20b may be made of the same or different materials (e.g., coil members 18a and 18b may include NiTi alloy (Nitinol) and coil members 20a and 20b may include stainless steel).

Figure 3B:
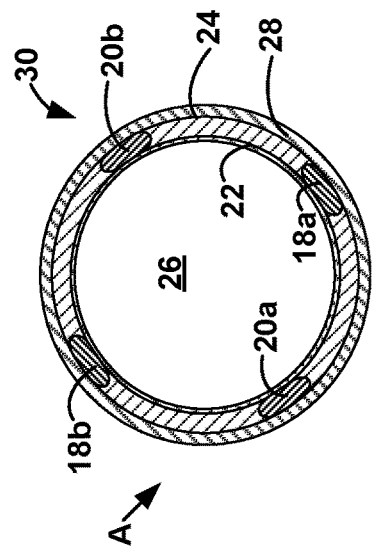
FIG. 3B is a conceptual radial cross-sectional view of the elongated body of FIG. 3A taken along line A-A in FIG. 3A.

FIG. 3B shows and radial cross-sectional view of elongated body 30 along line A-A of FIG. 3A. As shown in FIG. 3B, the number of coil members 18a, 18b, 20a, and 20b present in elongated body 30 may directly correspond to the number of coil members present in the radial cross-section of elongated body 30. Thus, increasing the number of coil members 18a, 18b, 20a, and 20b present in elongated body 30 will increase the amount of coils and the distribution of the coil members present in the radial cross-section of elongated body 30. In some examples, the greater the presence of coil members in the radial cross-section of elongated body 30, the higher the stiffness of elongated body 12 and, therefore, the higher the columnar strength of elongated body 12 in that particular portion. As shown in FIG. 3B, coil members 18a and 18b are positioned on radially opposite sides of elongated body 12 (e.g., 180° to one another). As discussed further with respect to FIGS. 6A-6B below, the position of coil members 18a and 18b relative to each other within the radial cross-section of elongated body 30 may be adjusted by increasing or decreasing one or more of the coil spacings (G) between coil members 18a, 18b, 20a, and 20b.

In some examples, the pitch (P) of the plurality of coil members may be varied along portions of the elongated body to tailor structural characteristics to select portions of the elongated body. For example, the proximal section of the elongated body (e.g., proximal portion 17A of elongated body 12) may include coil members that define a relatively short pitch (P) (e.g., as shown in FIGS. 4A and 4B) to increase the amount of coil material present in the radial cross-section of the elongated body, while the coil members in the distal portion of the elongated body (e.g., distal portion 17B of elongated body 12) may define a relatively long pitch (P) (e.g., as shown in FIGS. 5A and 5B), to decrease the amount of coil material present in the radial cross-section of the elongated body.

Figure 4A:
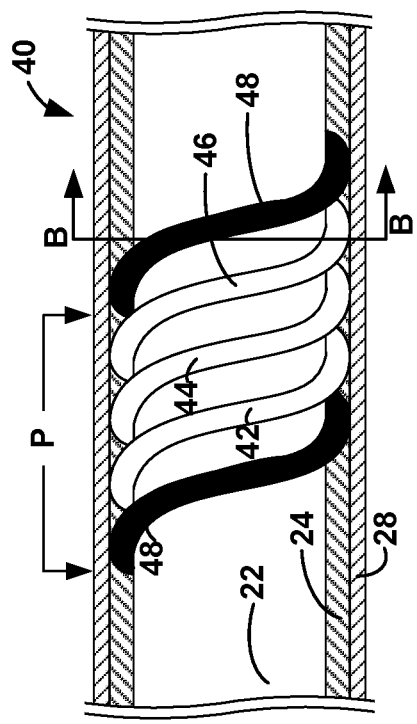
FIG. 4A is a conceptual axial cross-sectional view of an example elongated body that includes four coil members defining a relatively short pitch.
Figure 4B:
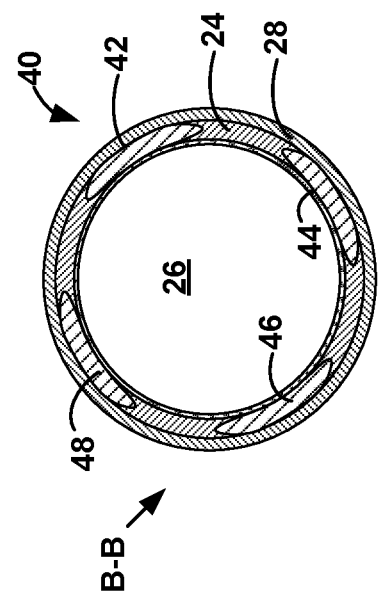
FIG. 4B is a conceptual radial cross-sectional view of the elongated body of FIG. 4A taken along line B-B in FIG. 4A.
Figure 5A:
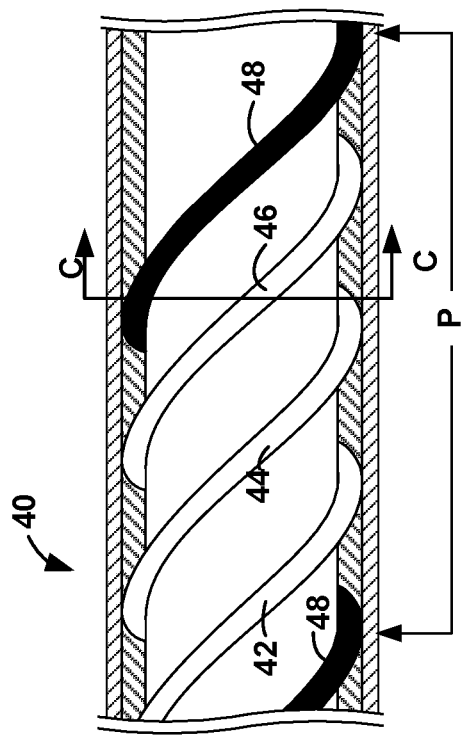
FIG. 5A is a conceptual axial cross-sectional view of an example elongated body that includes four coil members defining a relatively long pitch.
Figure 5B:
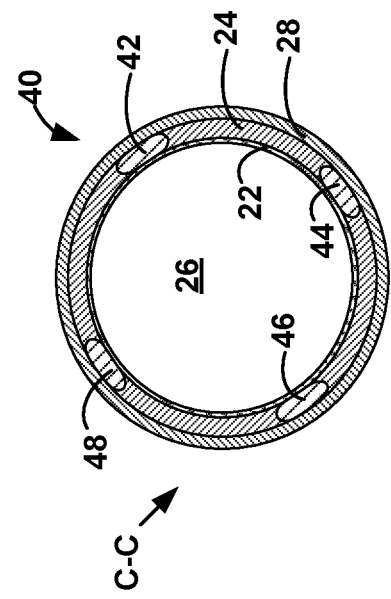
FIG. 5B is a conceptual radial cross-sectional view of the elongated body of FIG. 5A taken along line C-C in FIG. 5A.

FIGS. 4A and 5A are conceptual axial cross-sectional views of an example elongated body 40 that includes four coil members 42, 44, 46, and 48 (collectively "coil members 42-48"). FIG. 4A illustrates coil members 42-48 each defining a relatively short pitch (P) between sequential turns of the respective coil while FIG. 5A illustrates coil members 42-48 each defining a relatively long pitch (P) between sequential turns of the respective coil. The relatively short pitch (P) of coil members 42-48 in FIG. 4A may increase the amount of coil material present in the radial cross section of elongated body 40. For example, as shown in FIG. 4B, which is radial cross-sectional view of elongated body 40 along line B-B of FIG. 4A, because coil members 42-48 define a relatively short pitch (P) between sequential turns in FIG. 4A, there is a larger radial component of each respective coil member that defines a greater amount/area of coil material in the radial cross-section of FIG. 4B. In contrast, FIG. 5B is the radial cross-sectional view along line C-C FIG. 5A, which includes coil members 42-48 that define a relatively long pitch (P) between sequential turns of the coil members. The longer pitch of coil members 42-48 in FIG. 5A correlates to the coil members 42-48 having a smaller radial component that defines a smaller amount/area of coil material in the radial-cross-section of FIG. 5B (e.g., the area of coil member 48 in FIG. 4B is represented as being larger than the area of coil member 48 in FIG. 5B).

In examples in which coil members 42-48 include metal materials (e.g., NiTi alloy wire and/or stainless steel), the relatively short pitch (P) between sequential turns of FIG. 4A may create a portion of elongated body 40 that remains relatively stiff allowing for increased pushability and manipulation at the proximal end of elongated body 40 by the clinician (e.g., proximal portion 17A of catheter 10), while the relatively long pitch (P) between sequential turns of FIG. 5A may allow for increased flexibility and maneuverability at the distal end of elongated body 40 (e.g., distal portion 17B of catheter 10).

Figure 6A:
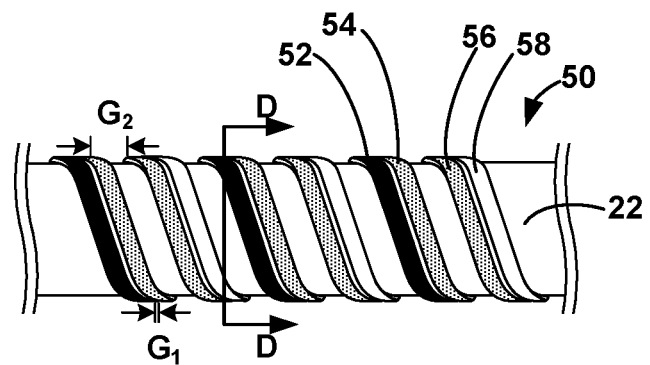
FIG. 6A is a conceptual axial cross-sectional view of an example elongated body that includes four coil members that define different coil spacings.

In some examples, the plurality of coil members may define one or more coil spacings (G) between adjacent turns of adjacent coils to vary the distribution of coil material in the radial cross-section of the elongated body. FIG. 6A is a conceptual axial cross-sectional view of an example elongated body 50 that includes a plurality of coil members 52-58 where the coil members define at least two different gap spacing (e.g., $G_1$ and $G_2$) between adjacent coil members.

Figure 6B:
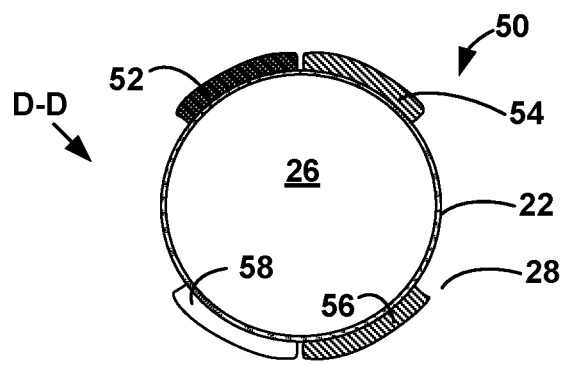
FIG. 6B is a conceptual radial cross-sectional view of the elongated body of FIG. 6A taken along line D-D in FIG. 6A.

Elongated body 50 includes four coil members 52, 54, 56, and 58 (collectively "coil members 52-58") wrapped around inner liner 22 (support layer 24 and outer jacket 28 are excluded for ease of illustration). Coil members 52 and 54 define a relatively short coil spacing ($G_1$) between sequential turns of respective coils, while coil members 54 and 56 define a relatively long coil spacing ($G_2$) between sequential turns of respective coils. FIG. 6B is a radial cross-sectional view of elongated body 50 along line D-D of FIG. 6A. As shown in FIG. 6B, the short coil spacing ($G_1$) and long coil spacing ($G_2$) alters the distribution of the coil members 52-58 in the radial-cross-section of FIG. 6B such that, for example, coil members 52 and 54 are grouped closely adjacent to one another about the 12-o'clock position of elongated body 50 shown in FIG. 6B while coil members 56 and 58 are grouped closely adjacent to one another about the 6-o'clock position of elongated body 50 shown in FIG. 6B. In some examples, including differing coil spacings (G) between the coil members 52-58 of elongated body 50 may allow the stiffness (or flexibility) to vary along the length of elongated body 50. For example, coil members 52 and 54 may be grouped closely adjacent to one another in the proximal portion of elongated body 50 to emulate a single, wide flat-wire coil, thereby providing increased stiffness depending on the materials used to form coil members 52 and 54.

Returning to FIG. 2, coil members 18 and 20 may be coupled, adhered and/or mechanically connected to at least a portion of an outer surface of inner liner 22 via an optional support layer 24. For example, support layer 24 may be a thermoplastic material or a thermoset material, such as a thermoset polymer and/or a thermoset adhesive (e.g., a thermoset polyurethane adhesive, such as Flexobond 430, commercially available from Bacon Industries of Irvine, Calif.). In some cases, the material forming support layer 24 may have elastic properties, such that there may be a tendency for support layer 24 to a return to a resting position. This may be referred to as "bounce back" of support layer 24. In some examples, support layer 24 may be formed from substantially the same material as inner liner 22 or outer jacket 28.

In some examples, the material that defines support layer 24 is provided by one or more filaments (e.g., coil members) interspaced with coil members 18 and 20, which are reformed (e.g., reflowed) during subsequent processing to form support layer 24. For example, coil members 18 and 20 may be simultaneously wrapped around inner liner 22 with filaments ("support filaments") formed from materials used to make supportive layer 24. Once the coils/filaments have been wrapped around inner liner 22, the support filaments may be subsequently heated to reflow some of the support filaments to form support layer 24. In such examples, the one or more support filaments that form support layer 24 may be used to define the coil spacing (G) between adjacent turns of coil members 18 and 20. Interspacing one or more support filaments among coil members 18 and 20 may allow for a more consistent and controlled pitch (P) of coil members 18 and 20 and/or coil spacing (G) between adjacent turns of coils members 18 and 20, which may provide greater structural consistency throughout elongated body 12. For example, rather than having to define the desired spacing of coil members 18 and 20 with voids between turns of coil members 18 and 20, into which coil members 18 and 20 may inadvertently move, the support filaments may fill one or more of the voids, such that the relative position of coil members 18 and 20 is set prior to forming support layer 24, which may help fix coil members 18 and 20 in place once support layer 24 has been fully formed.

Support layer 24 may include any suitable material. In some examples, support layer 24 may be formed from substantially the same material as inner liner 22 or outer jacket 28 including, for example, polytetrafluoroethylene (PTFE), a fluoropolymer, a polyolefin, perfluoroalkyoxy alkane (PFA), fluorinated ethylene propylene (FEP), or any combination thereof In some examples, support layer 24 may be formed from a cured thermoset polyurethane adhesive, which may exhibit a relatively delayed bounce back response compared to a thermoplastic material, e.g., due at least in part to the elastic properties of the thermoset polyurethane adhesive. The delayed bounce back response may be advantageous for navigating elongated body 12 through the vasculature of a patient. For example, the delayed bounce back response may reduce the extent to which elongated body 12 may spring against vascular walls as it is advanced through the vasculature. In addition, due the properties of a thermoset polyurethane adhesive or other thermoset polymer, the thermoset polymer may not reflow after support layer 24 is formed, e.g., during the application of heat when outer jacket 28 is applied over coil members 18 and 20 and support layer 24. Thus, the thermoset polymer may help coil members 18 and 20 remain substantially in place, with the desired pitch and gap spacing, during subsequent manufacturing steps.

In some examples, support layer 24 may not be present such that the layer defined by support layer 24 and coil members 18 and 20 is formed primarily of a plurality of coil members 18 and 20. In some examples, support layer 24 may be formed as a result of forming outer jacket 28 over coil members 18 and 20. For example, outer jacket 28 may be heat shrunk onto coil members 18 and 20 filling the voided space between coil members 18 and 20 with material from outer jacket 28.

In some examples, support layer 24 may encase or partially encase coil members 18 and 20 so that the coil members do not substantially directly contact inner liner 22 and/or outer jacket 28. For example, coil members 18 and 20 may include cladded wires such as a metal filament coated with a thermoplastic polymer. Once coil members 18 and 20 are positioned over inner liner 22, coil members 18 and 20 may be heated to reflow part of the polymer coating to form support layer 24 with embedded metal wires.

In other examples, support layer 24 may only be positioned between coil members 18 and 20 and inner liner 22, and substantially no support layer 24 material (e.g., no support layer material or nearly no support layer material) is positioned between coil members 18 and 20 and outer jacket 28. For example, a thermoset polymer may be applied to the outer surface of inner liner 22 prior to positioning coil members 18 and 20 over inner liner 22. The thermoset polymer may then be cured to fix coil members 18 and 20 to inner liner 22 wherein the thermoset polymer forms a layer (e.g., support layer 24) between coil member 18 and 20 and inner liner 22. Outer jacket 28 then may be heat shrunk onto coil members 18 and 20 and support layer 24, which may eliminate the need for an adhesive to further mechanically connect outer jacket 28 to coil members 18 and 20 and support layer 24. As a result, coil members 18 and 20 and inner liner 22 may not be adhered to outer jacket 28. In at least this way, the use of a thermoset polymer may also at least partially fill the gap distance between coil members 18 and 20 to prevent longitudinal movement of the coils.

In the example shown in FIG. 2, substantially no material (e.g., no material or nearly no material) is present between at least some portions of coil members 18 and 20 and at least some portions of outer jacket 28, such that at least a portion of coil members 18 and 20 is in direct contact with outer jacket 28. This direct contact may help distribute flexibility from coil members 18 and 20 to outer jacket 28, which may increase the kink resistance of elongated body 12. Such examples may help reduce the thickness of catheter body wall (T), which may help increase the inner diameter (ID) of inner lumen 26 for a given outer diameter (OD) of elongated body 12. As discussed, a larger inner lumen 26 may provide certain benefits in some examples, such as allowing for more effective aspiration of thrombi, for accommodation of a larger range of medical devices or easier manipulation of medical devices within inner lumen 26, or both.

In addition to helping to reduce the thickness T of the wall of elongated body 12, a thermoset polymer may provide better structural integrity to elongated body 12 compared to a thermoplastic polymer. In contrast some or all thermoplastic polymers, a thermoset polymer may include polymers that cross-link together during the curing process. This cross-linking may provide a particular sample of a thermoset polymer with higher temperature resistance, more flexibility, and more dimensional stability compared to a sample of a thermoplastic material having the same dimensions. The higher flexibility and higher dimensional stability may help achieve the desired structural characteristics for elongated body 12, e.g., the desired flexibility, kink-resistance, and pushability.

In some examples, support layer 24 may be configured to fill at least part of the spaces between portions of coil members 18 and 20, e.g., the volume defined within coil spacings (G). The presence of support layer 24 between turns of coil members 18 and 20 may help distribute the flexibility provided by coil members 18 and 20 along the length of coil members 18 and 20, which may help prevent elongated body 12 from kinking. For example, at least by eliminating voids between turns of coil members 18 and 20, support layer 24 may transfer the flexing motion from coil members 18 and 20 along a length of elongated body 12.

In some examples, in addition to changing stiffness along the length of coil members 18 and 20, coil members 18 and 20 may change in coil diameter along a length of elongated body 12. For example, coil members 18 and 20 may taper from a first coil diameter to a second coil diameter to mirror the tapper of inner liner 22 (if present).

In some examples, respective coil members 18 and 20 may each be formed from a segmented filament that extends from proximal end 12A to distal end 12B of elongated body 12. The segmented filament may be substantially seamless such that the joint between the segments of the filament that are connected together to define a relatively smooth transition between the segments of the filament. The segments of the filaments may include different materials such as to tailor the structural characteristics of the filament to select portions of elongated body 12. In some examples, defining coil members 18 and 20 from a single, seamless filament (e.g., a continuous filament) may increase the structural integrity of elongated body 12 compared to examples in which members 18 and 20 is formed from multiple filaments that are joined together. For example, the joints between filaments may adversely affect the tensile strength or lateral flexibility of members 18 and 20, which may adversely affect the flexibility and pushability of elongated body 12.

In other examples, one or more coil members 18 and 20 may extend only partially along the length of elongated body 12. For example, first coil member 18 may extend from proximal end 12A along only proximal portion 17A while second coil member 20 extends along the entire length of elongated body 12. In this way, coil members of different constructions may be included in select portions of elongated body 12 to define different structural characteristics (e.g., enhanced flexibility) for different portions of elongated body 12. In some examples, multiple coil members 18 and 20 may be wound along the length of elongated body 12 and selectively removed from portions of elongated body 12 one or more of the coil members through cutting, chemically etching, dissolving, or the like the one or more coil members. For example, second coil member 20 may be selectively removed or partially removed via, for example, chemical etching from distal portion 17B of elongated body 12 to increase the flexibility of distal portion 17B compared to proximal portion 17A.

In some examples, coil members 18 and 20 do not extend all the way to distal end 12B of elongated body 12, but, rather, end at a point that is proximal to the distal end 12B. For example, coil members 18 and 20 may end about 0.25 mm to about 1 mm, such as about 0.5 mm, from distal end 12B. Thus, coil members 18 and 20 may not contribute to the structural integrity of a distal-most portion of elongated body 12. In such examples, elongated body 12 may include a distal tip (not shown) configured to help navigate and/or provide structural support for distal end 12B of elongated body 12 as the end is advanced through the vasculature of a patient.

As shown in FIG. 2, catheter 10 also includes outer jacket 28, which may be positioned radially outward of inner liner 22 and coil members 18 and 20, and, in some examples, define the outer surface of elongated body 12. Although a coating or another material may be applied over the outer surface of outer jacket 28, outer jacket 28 may still substantially define shape and size of the outer surface of elongated body 12. Outer jacket 28, together with coil members 18 and 20 and inner liner 22, may be configured to define elongated body 12 having the desired flexibility, kink resistance, torque responsiveness, structural integrity, and pushability characteristics.

Outer jacket 28 may have stiffness characteristics that contribute to the desired stiffness profile of elongated body 12. For example, outer jacket 28 may be formed to have a stiffness that decreases from a proximal portion of elongated body 12 to a distal portion. For example, outer jacket 28 may be formed from two or more different materials that enable outer jacket 28 to exhibit the desired stiffness characteristics. In some examples, outer jacket 28 and coil members 18 and 20 may be selected such that outer jacket 28 has a higher durometer than coil member 18 and 20. In some examples, outer jacket 28 may be define a durometer gradient along longitudinal axis 16. For example outer jacket 28 may be defined by a plurality of tubular segments extending from proximal end 12A to distal end 12B wherein each tubular segment defines a different durometers. The durometers gradient of outer jacket 28 may be selected to help provide elongated body 12 with the desired flexibility characteristics. For example, in some examples in which elongated body 12 increases in flexibility from proximal end 12A towards distal end 12B, the durometer gradient of outer jacket 28 may decrease in a direction from proximal end 12A towards distal end 12B. In some examples, the durometer gradient of outer jacket 28 may decrease in a direction from proximal end 12A towards distal end 12B and then increase just proximate of distal end 12B to provide an increased flexibility about distal portion 17B while also increasing the hardness about distal opening 13 to resist geometric deformation when distal opening 13 (FIG. 1) of elongated body 12 is engaged with a guidemember, which may help support the navigation of elongated body 12 through vasculature. In some examples, the durometer of outer jacket 28 may be from about 25D to about 75D. For example, outer jacket may define a durometer gradient from proximal end 12A towards distal end 12B that generally decreases from about 75D to about 25D, with a distal segment defining distal opening 13 having a durometer greater than 25D (e.g., 55D).

Example materials that may be used to form outer jacket 28 include, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, S.C.), another thermoplastic elastomer or other thermoplastic material, or combinations thereof In some examples, at least a portion of an outer surface of outer jacket 28 includes one or more coatings, such as, but not limited to, an anti-thrombogenic coating, which may help reduce the formation of thrombi in vitro, an antimicrobial coating, and/or a lubricating coating. The lubricating coating may be configured to reduce static friction and/or kinetic friction between elongated body 12 and tissue of the patient as elongated body 12 is advanced through the vasculature of the patient. The lubricating coating can be, for example, a hydrophilic coating. In some examples, the entire working length of elongated body 12 (from distal portion 14B of hub 14 to distal end 12B) may be coated with the hydrophilic coating. In other examples, only a portion of the working length of elongated body 12 coated with the hydrophilic coating. This may provide a length of elongated body 12 distal to distal end 14B of hub 14 with which the clinician may grip elongated body 12, e.g., to rotate elongated body 12 or push elongated body 12 through the vasculature of the patient.

Figure 7:
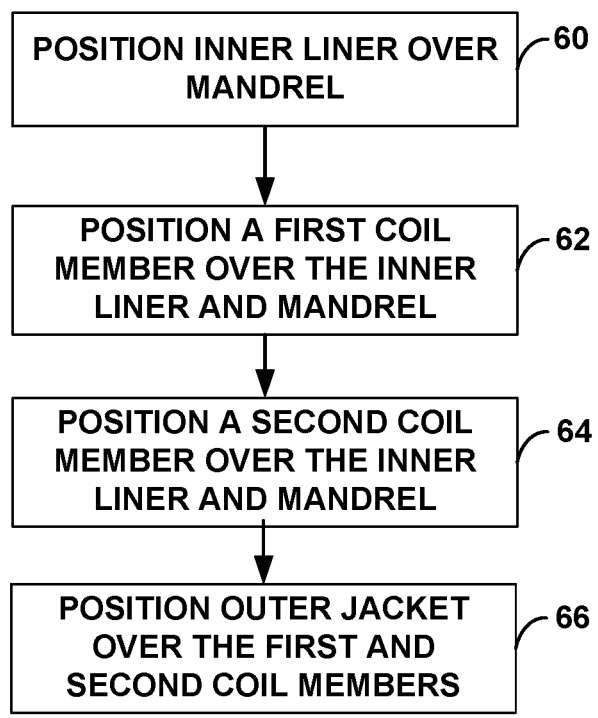
FIG. 7 is a flow diagram of an example method of forming the catheter of FIG. 1.

The catheters described herein can be formed using any suitable technique. FIG. 7 is a flow diagram of an example method of forming catheter 10, and is described with reference to FIGS. 8 and 9, which are schematic side elevation views of assemblies after some steps of the methods. In accordance with the technique shown in FIG. 7, inner liner 22 may be positioned over mandrel 70 (60). In some examples, inner liner 22 is a unitary, seamless body, and may be positioned over mandrel 70 by at least inserting mandrel 70 through lumen 26 of inner liner 22.

Figure 8:
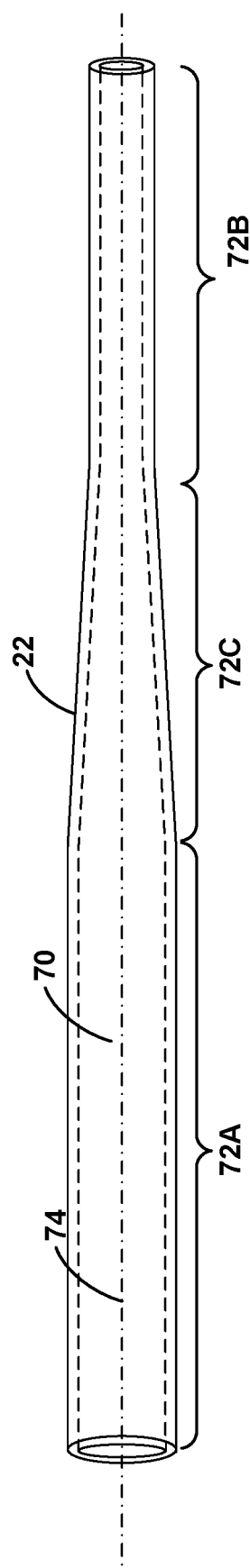
FIG. 8 is a schematic side elevation view of an example mandrel and an example inner liner positioned over the mandrel.

As discussed above, in some examples, elongated body 12 may tapers from proximal portion 17A (FIG. 1) having a first outer diameter to distal portion 17B having a second outer diameter, e.g., along medial portion 17C, which continuously tapers from the first outer diameter to the second outer diameter. In these examples, mandrel 70 may define a corresponding change in outer diameter. For example, as shown in FIG. 8, mandrel 70 includes proximal portion 72A having a first mandrel outer diameter that is substantially constant (e.g., constant or nearly constant, except for minor manufacturing variances) along proximal portion 72A, distal portion 72B having a second mandrel outer diameter that is substantially constant along distal portion 72B, and medial portion 72C, which continuously tapers from the first mandrel outer diameter to the second mandrel outer diameter.

The length (measured in a direction parallel to a longitudinal axis 74 of mandrel 70) of each of potions 72A-72C may be selected based on the desired length of proximal, distal, and medial portions 17A-17C, respectively, of elongated body 12. For example, medial portion 72C may have a length of about length of about 1 inch (about 2.5 cm) to about 3 inches (about 7.6 cm), such as about 2 inches (about 5 cm).

In other examples, mandrel 70 may define a substantially constant (e.g., constant or nearly constant) outer diameter portion for forming elongated body 12 having a substantially constant outer diameter from proximal end 12A to distal end 12B.

Mandrel 70 may be formed from any suitable material. The material from which mandrel 70 is formed may be configured to relatively easily release inner liner 22, e.g., after elongated body 12 is formed over mandrel 70. For example, mandrel 70 may be formed from an extruded PTFE (e.g., mandrel 70 may consist of or consist essentially of an extruded PTFE).

In some examples, in the technique shown in FIG. 7, after positioning inner liner 22 over mandrel 70, inner liner 22 may be heat shrunk onto mandrel 70 and may, as a result, conform to the outer surface of mandrel 70 and acquire the tapered profile of mandrel 70. For example, inner liner 22 may have a somewhat larger inner diameter than mandrel 70 in order to permit inner liner 22 to be relatively easily slipped over one end of mandrel 70. In other examples, however, heat shrinking may not be necessary. For example, in addition to, or instead of, heat shrinking, inner liner 22 may be longitudinally stretched over mandrel 70 in order to substantially conform to the outer surface of mandrel 70. In either example, inner liner 22 may define a constant inner diameter or may have different inner diameters, e.g., corresponding to the outer diameters defined by mandrel 70.

In examples in which mandrel 70 defines an outer diameter that changes over a length of mandrel 70, when inner liner 22 is positioned over mandrel 70 and substantially conforms to an outer surface of mandrel 70, inner liner 22 may be acquire the profile of mandrel 70. Thus, mandrel 70 helps to define inner liner 22 that includes a proximal inner lumen portion having a first inner lumen diameter, a distal inner lumen portion having a second inner lumen diameter, and a medial inner lumen portion that gradually tapers in diameter from the first inner lumen diameter to the second inner lumen diameter.

Figure 9:
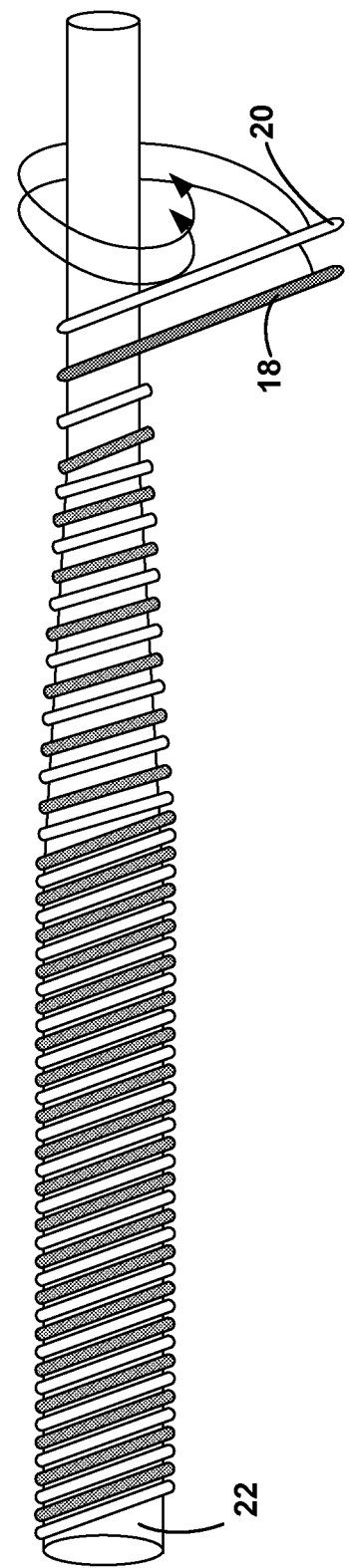
FIG. 9 is a schematic side elevation view of example coil members positioned over an inner liner.

After positioning inner liner 22 over mandrel 70 (60), first coil member 18 may be positioned over inner liner 22 (62) and second coil member 20 may also be positioned over inner liner 22 (64), as shown in FIG. 9. Coil members 18 and 20 may each be wound over an outer surface of inner liner 22 or pushed over inner liner 22. In some examples first coil member 18 and second coil member 20 may be positioned over inner liner 22 at the same time. For examples, coil members 18 and 20 may be simultaneously wound or pushed over the outer surface of inner liner 22. In other examples, first coil member 18 and second coil member 20 may be positioned over inner liner 22 at separate times.

In some examples, the structural configuration of coil members 18 and 20 may be at least partially defined prior to being positioned over inner liner 22. For example, a shape memory wire (e.g., NiTi alloy) or a wire of an otherwise heat-settable metal, alloy, or polymer base may be wound over a different mandrel (e.g., a "coil mandrel") on which inner liner 22 is not present or over mandrel 70 (e.g., before inner liner 22 is positioned on mandrel 70) to define at least one of the desired coil pitch (P), the desired coil diameter, the desired tapering profile (e.g., a continuous tapering or progressive tapering), the desired coil spacing (G), or the desired length of coil members 18 and 20, and then heat set to substantially hold its shape. In some examples, one or more coil member 18 and 20 may be wound on a coil mandrel interspaced with a spacer material (e.g., dissolvable polymer, such as nylon or polyethylene) that is used to define coil spacings (G). For example, for a single coil construction, the spacer material may be wound in direct contact with the coil member 18. The spacer material may define a thickness equal to the intended gap distance between adjacent turns of coil member 18. After winding and heat setting coil member 18 on mandrel 70 and or inner liner 22, the spacer material may then be removed through, for example, chemical etching leaving behind coil member 18 with a well-defined gap distance between adjacent turns. As another example, the spacer material may be a material that is used to form support layer 24, for example the spacer material may be reflowed to define support layer 24.

After being heat set, the coil members 18 and 20 may then be subsequently unwound from the mandrel onto a reel or a bobbin (not shown), and then positioned over inner liner 22. Defining some or all of the structural characteristics of coil members 18 and 20 prior to positioning the respective coil members over inner liner 22 may help control the structural characteristics of coil members 18 and 20 (e.g., gap spacings (G) and pitch (P)), as well as control product consistency and uniformity of the coil members 18 and 20 used in multiple catheters. Pre-shaping and shape-setting the coil members 18 and 20 as a coil (as opposed to ordinary wire stock) may cause coil members 18 and 20 to conform closely to the inner liner 22 as the members 18 and 20 are wound onto the liner 22. This close conformance may help reduce the wall thickness T in the elongated body 12. In addition, shape-setting the coil members 18 and 20 on a separate, heat-resistant mandrel enables the construction of the elongated body 12 using the member 20 on a mandrel made of PTFE or other lubricious, non-heat resistant material.

In some examples, once positioned over inner liner 22, the layout of the respective coil members 18 and 20 may be adjusted to achieve the desired pitch profile (e.g., the change in pitch over the length) and coil spacings (G) coil members 18 and 20. In some examples, simultaneously positioning coil members 18 and 20 on inner liner 22 may help to maintain a more consistent gap spacing (G) and/or pitch profile. The structural configuration of coil members 18 and 20 may be at least partially defined as the coils are wound over inner liner 22 to define the desired coil pitch, taper, and coil spacings. In examples in which one or more of coil members 18 and 20 are made from shape memory material, the coils may be subsequently heated after being positioned on inner liner 22 to heat set the coil.

Coil members 18 and 20 may be secured in place relative to inner liner 22 using any suitable technique. For example, coil members 18 and 20 may be adhered to inner liner 22. In some examples, an adhesive and/or a polymer is applied to coil members 18 and 20 are positioned over inner liner 22. In other examples, an adhesive may be positioned over inner liner 22 prior to positioning coil members 18 and 20 over inner liner 22. In addition to, or instead of, an adhesive, outer jacket 28 may be used to secure coil members 18 and 20 to inner liner 22.

In examples in which one or more of coil members 18 and 20 are in the form of a cut hypotube, the hypotube may be defined to have a diameter less than the diameter of inner liner 22. As the hypotube is positioned on inner liner 22, the diameter of the hypotube may be expanded thereby creating the gap distance between adjacent turns of the hypotube, which may receive one or more other coil members in the created spacing.

While only two coil members 18 and 20 are shown in FIGS. 2 and 9, in some examples coil members 18 and 20 may include more than two coil members made from different materials. For example, elongated body 12 may comprise multiple first coil members 18 formed from a NiTi alloy and multiple second coil members 20 formed from stainless steel.

As noted above, in some examples, elongated body 12 may include support layer 24. In some examples, additional coil members may be present interspaced with first and second coil members 18 and 20 to assist with defining the coil spacings between first and second coil members 18 and 20. For example, coil members 18 and 20 may be wrapped with coils made of material used to form support layer 24 to define substantially consistent coil spacings throughout portions of elongated body 12. In some examples, the support layer 24 material may be substantially the same (e.g., the same or nearly the same) as inner liner 22 or outer jacket 28 such that the material may be heated to partially reflow and join (e.g., thermoplastic polymer) with the respective inner liner 22 or outer jacket 28.

In other examples, support layer 24 may be formed from a thermoset polymer, which may be applied to an outer surface of inner liner 22 after inner liner 22 is positioned over mandrel 70 but before coil members 18 and 20 are positioned over inner liner 22. First and second coil members 18 and 20 may then be positioned over inner liner 22 and the thermoset polymer (62 and 64). At least some of the thermoset polymer may be displaced by coil members 18 and 20 when the coils are positioned over inner liner 22, which may cause at least some of the thermoset polymer to be positioned between the turns of the respective coil members 18 and 20. In some examples, support layer 24 may include a thermoset polymer. The thermoset polymer may be, for example, a viscoelastic thermoset polyurethane (e.g., Flexobond 430).

The thermoset polymer may be configured to be time cured and/or heat cured, such that the adhesive may not substantially immediately fix the position of coil members 18 and 20 relative to inner liner 22. As a result, in some examples, the pitch of the coil (e.g., along the medial portion 32 (FIG. 5)) may be adjusted after member 20 is positioned over inner liner 22 and the thermoset polymer. In accordance with the technique shown in FIG. 7, after coil members 18 and 20 is positioned over inner liner 22 and the thermoset polymer (62 and 64), the thermoset polymer is cured e.g., by heating and/or time-curing to define support layer 24. In some examples, such as some examples in which the thermoset polymer is a thermoset polyurethane, the subassembly including mandrel 70, inner liner 22, the thermoset polymer, and coil members 18 and 20 may be heat cured, e.g., at a temperature of about 200 degrees Fahrenheit (° F.) (about 93.33 degrees Celsius (° C.)) for about two hours.

In the technique shown in FIG. 7, after coil members 18 and 20 are positioned over inner liner 22 (62 and 64), outer jacket 28 is positioned over an outer surface of coil members 18 and 20 (66). In some examples, outer jacket 28 is adhered to an outer surface of coil members 18 and 20, e.g., an adhesive/polymer may be applied to outer surface of coil members 18 and 20 prior to positioning outer jacket 28 over the coils and then cured after outer jacket 28 is positioned. In some examples, the adhesive/polymer may be applied as a coil member interspaced with coil members 18 and 20 that is subsequently reflowed to adhere outer jacket 28 to coil members 18 and 20 and inner liner 22. In addition to, or instead of, the adhesive, outer jacket 28 may be heat shrunk over coil members 18 and 20 and inner liner 22. In some examples, the heat shrinking of outer jacket 28 may help secure the respective positions of coil members 18 and 20 along elongated body 12.

The use of heat shrinking to apply outer jacket 28 to the subassembly including inner liner 22, support layer 24, and coil members 18 and 20 may help eliminate the need for an adhesive between coil members 18 and 20 and outer jacket 28. This may help minimize the wall thickness of elongated body 12 and, therefore, increase the inner diameter of elongated body 12 for a given outer diameter. In addition, the absence of an adhesive layer adhering support layer 24 and coil members 18 and 20 to outer jacket 28 may contribute to an increased flexibility of catheter body 22.

Once elongated body 12 is formed, hub 14 may be attached to proximal end 14A of elongated body 12 using any suitable technique, such as an adhesive, welding, or any combination thereof In some examples, catheter 10 or elongated body 12 may be a part of an assembly that includes, e.g., a guidemember and/or another catheter. The catheter 10 or elongated body 12 in such an assembly can be any of the examples of the catheter 10 or elongated body 12 disclosed herein. The guidemember may be used to guide catheter 10 to a target tissue site within the vasculature of a patient. In addition, in some examples, the additional catheter of the assembly may also be configured to guide catheter 10 or body 12 to a target tissue site within the vasculature of a patient. The additional catheter of the assembly may be substantially similar (e.g., identical or nearly identical) in construction to catheter 10 (including any of the examples of the catheter 10 disclosed herein), but may have proportionally greater or smaller dimensions, such that the catheter bodies of the catheters may nest together. For example, the additional catheter of the assembly may have a smaller outer diameter than elongated body 12 and may be placed and/or guided over the guidemember, and then catheter 10 or elongated body 12 may be guided over the additional catheter. If, for example, catheter 10 or body 12 tapers from a 6 French outer diameter to a 5 French outer diameter, then the additional catheter may taper from a 4 French outer diameter to a 3 French outer diameter. The assembly may therefore comprise the catheter 10 with the additional catheter positioned in the inner lumen 26 of the catheter, and may further comprise the guidemember positioned in the inner lumen of the additional catheter.

Each of the components of the assembly may be slidably disposed relative to the other(s) so that each may be advanced and/or retracted over or within the other(s). For example, when the additional catheter is positioned in the lumen of the catheter 10, the catheter 10 may be advanced or retracted longitudinally over the additional catheter, and/or the additional catheter can be advanced or retracted longitudinally within the catheter 10. The use of the additional catheter in this manner may help reduce any adverse interactions with tissue attributable to the ledge effect. For example, if in use of an assembly having a guidemember the guidemember is first advanced into the vasculature, the additional catheter may next be advanced over the guidemember before the catheter 10 is advanced over the additional catheter. The difference in outer diameter between the guidemember and the additional catheter (and between the additional catheter and the catheter 10) is less than the difference in outer diameter between the guidemember and the catheter 10. Therefore, any ledge effect arising from advancing the catheter 10 over a "bare" guidemember may be mitigating by use of the additional catheter in this manner. In other examples, the additional catheter of the assembly may have a larger outer diameter than catheter 10 or body 12 and may be guided over catheter 10 or body 12 to a target tissue site within the vasculature of the patient. If, for example, catheter 10 or body 12 tapers from a 4 French outer diameter to a 3 French outer diameter, then the additional catheter may taper from a 6 French outer diameter to a 4 French outer diameter.

In some examples, a method of using catheter 10 comprises introducing a guidemember or an inner catheter into vasculature (e.g., an intracranial blood vessel) of a patient via an access point (e.g., a femoral artery), and guiding elongated body 12 over the guidemember or the inner catheter. Once distal end 12B of elongated body 12 is positioned at the target tissue site, which may be proximal to thromboembolic material (e.g., a thrombus), the thromboembolic material be removed from the vasculature via elongated body 12. For example, the thromboembolic material may be aspirated from the vasculature by at least applying a vacuum force to inner lumen 26 of elongated body 12 via hub 14 (and/or proximal end 12A), which may cause the thromboembolic material to be introduced into inner lumen 26 via distal opening 13. Optionally, the vacuum or aspiration can be continued to thereby draw the thromboembolic material proximally along the inner lumen 26, all or part of the way to the proximal end 12A or hub 14. As another example, the thromboembolic material may be removed from the vasculature using another technique, such as via an endovascular retrieval device delivered through the inner lumen 26 of the elongated body 12. In such a method the elongated body 12 can be inserted into the vasculature (for example using any technique disclosed herein) and the retrieval device advanced through the inner lumen 26 (or through another catheter, such as a microcatheter, inserted into the vasculature through the inner lumen 26) so that the device engages the thromboembolic material. The retrieval device and the material engaged thereby (together with any other catheter or microcatheter) can then be retracted into the inner lumen 26 and removed from the patient. Optionally, aspiration can be performed with or through the elongated body 12 during retraction of the retrieval device and thromboembolic material into the elongated body 12. The vasculature can comprise the neurovasculature, peripheral vasculature or cardiovasculature. The thromboembolic material may be located using any suitable technique, such as fluoroscopy, intravascular ultrasound or carotid Doppler imaging techniques.

Various examples have been described. These and other examples are within the scope of the following claims.

What is claimed is:

1. A catheter comprising:
   an elongated body comprising:
      a first coil member;
      a second coil member interspaced with the first coil member, the first and second coil members comprising different materials, wherein the first and second coil members each define a plurality of turns, all the turns of the first and second coil members winding in a same direction; and
      an outer jacket positioned over the first and second coil members and securing the first and second coil members in place,
      wherein turns of the first coil member and turns of the second coil member are longitudinally offset from each other, and wherein the offset defines a first coil spacing along a proximal portion of the elongated body and a second coil spacing along a distal portion of the elongated body, the second coil spacing being different than the first coil spacing.

2. The catheter of claim 1, wherein at least one turn of the second coil member is positioned between adjacent turns of the first coil member.

3. The catheter of claim 1, wherein the first coil member contacts the second coil member.

4. The catheter of claim 1, wherein the first coil spacing is less than the second coil spacing.

5. The catheter of claim 1, wherein the first coil member and the second coil member have substantially same pitches.

6. The catheter of claim 1, wherein the catheter comprises a plurality of coil members, the plurality including the first and second coil members, and further comprising at least one additional coil member formed from a same material as the first coil member.

7. The catheter of claim 1, wherein the second coil member is interspaced with only a portion of the first coil member.

8. The catheter of claim 1, wherein the first and second coil members are formed from materials having different elasticities.

9. The catheter of claim 1, further comprising an inner liner defining an inner lumen of the elongated body, the first and second coil members being positioned between the inner liner and the outer jacket.

10. The catheter of claim 9, wherein the first and second coil members are each directly adjacent to the inner liner.

11. The catheter of claim 1, wherein the first and second coil members do not cross or overlap each other.

12. The catheter of claim 1, wherein at least three turns of the second coil member are interspaced between turns of first coil member.

13. The catheter of claim 1, wherein the first and second coil members have different pitches.

14. A catheter comprising:
    an elongated body comprising:
        a first coil member;
        a second coil member interspaced with the first coil member, the first and second coil members comprising different materials, wherein the first and second coil members each define a plurality of turns, all the turns of the first and second coil members winding in a same direction; and
        an outer jacket positioned over the first and second coil members and securing the first and second coil members in place, wherein the first and second coil members have different pitches.

15. A catheter comprising:
    an elongated body comprising:
        a structural support layer comprising at least a first filament and a second filament, the first and second filaments comprising different materials and wound longitudinally adjacent to each other to define a coil structure, wherein the first and second filaments each define a plurality of turns, all the turns of the first and second filaments winding in a same direction; and
    an outer jacket positioned over the structural support layer and securing the first and second filaments in place,
    wherein turns of the first filament and turns of the second filament are longitudinally offset from each other, and wherein the offset defines a first gap distance along a proximal portion of the elongated body and a second gap distance along a distal portion of the elongated body, the second gap distance being different than the first gap distance.

16. The catheter of claim 15, wherein the coil structure includes alternating turns of the first and second filaments.

17. The catheter of claim 15, wherein the coil structure includes more turns of the first filament than the second filament.

18. The catheter of claim 15, wherein the first filament comprises a plurality of first filaments.

19. The catheter of claim 15, further comprising an inner liner defining an inner lumen of the elongated body, the first and second filaments being wound around the inner liner and positioned between the inner liner and the outer jacket.

20. The catheter of claim 15, wherein at least one turn of the second filament is positioned between adjacent turns of the first filament.

21. The catheter of claim 15, wherein the first filament contacts the second filament.

22. The catheter of claim 15, wherein the first gap distance is less than the second gap distance.

23. The catheter of claim 15, wherein the first filament and the second filament have substantially same pitches.

24. The catheter of claim 15, wherein the first and second filaments have different pitches.

25. The catheter of claim 15, wherein the catheter comprises a plurality of filaments, the plurality including the first and second filaments, and further comprising at least one additional filament formed from a same material as the first filament.

26. The catheter of claim 15, wherein at least three turns of the second filament are interspaced between turns of the first filament.

* * * * *